United States Patent
Roquet et al.

(10) Patent No.: US 11,535,842 B2
(45) Date of Patent: Dec. 27, 2022

(54) NUCLEIC ACID SECURITY AND AUTHENTICATION

(71) Applicant: CATALOG TECHNOLOGIES, INC., Charlestown, MA (US)

(72) Inventors: Nathaniel Roquet, Charlestown, MA (US); Hyunjun Park, Charlestown, MA (US); Swapnil P. Bhatia, Charlestown, MA (US); Devin Leake, Charlestown, MA (US)

(73) Assignee: CATALOG TECHNOLOGIES, INC., Charlestown, MA (US)

( * ) Notice: Subject to any disclaimer, the term of this patent is extended or adjusted under 35 U.S.C. 154(b) by 0 days.

(21) Appl. No.: 17/069,420

(22) Filed: Oct. 13, 2020

(65) Prior Publication Data

US 2021/0108194 A1    Apr. 15, 2021

Related U.S. Application Data

(60) Provisional application No. 62/914,086, filed on Oct. 11, 2019.

(51) Int. Cl.
| | |
|---|---|
| *C12N 15/10* | (2006.01) |
| *G06N 3/00* | (2006.01) |
| *G06N 3/12* | (2006.01) |
| *H04L 9/08* | (2006.01) |
| *H04L 9/32* | (2006.01) |

(52) U.S. Cl.
CPC ......... *C12N 15/1065* (2013.01); *G06N 3/002* (2013.01); *G06N 3/123* (2013.01); *H04L 9/0869* (2013.01); *H04L 9/3213* (2013.01)

(58) Field of Classification Search
CPC .... C12N 15/1065; G06N 3/002; G06N 3/123; H04L 9/0869; H04L 9/3213; C12Q 1/6869
See application file for complete search history.

(56) References Cited

U.S. PATENT DOCUMENTS

| | | |
|---|---|---|
| 5,821,886 A | 10/1998 | Son |
| 6,030,657 A | 2/2000 | Butland et al. |
| 6,187,537 B1 | 2/2001 | Zinn, Jr. et al. |
| 6,221,653 B1 | 4/2001 | Caren et al. |
| 6,309,828 B1 | 10/2001 | Schleifer et al. |
| 6,384,210 B1 | 5/2002 | Blanchard |
| 6,419,883 B1 | 7/2002 | Blanchard |
| 6,446,642 B1 | 9/2002 | Caren et al. |
| 6,458,583 B1 | 10/2002 | Bruhn et al. |
| 6,537,747 B1 | 3/2003 | Mills, Jr. et al. |
| 6,796,634 B2 | 9/2004 | Caren et al. |
| 7,176,297 B2 | 2/2007 | Li et al. |
| 7,306,316 B2 | 12/2007 | Doak |
| 7,491,422 B2 | 2/2009 | Zhang et al. |
| 7,600,840 B2 | 10/2009 | Kim et al. |
| 7,802,517 B2 | 9/2010 | Wessels et al. |
| 7,833,701 B2 | 11/2010 | Oshima |
| 7,909,427 B2 | 3/2011 | Kim et al. |
| 7,951,334 B2 | 5/2011 | Mirkin et al. |
| 8,071,168 B2 | 12/2011 | Cruchon-Dupeyrat et al. |
| 8,114,207 B2 | 2/2012 | Josten |
| 8,136,936 B2 | 3/2012 | Hook et al. |
| 8,496,326 B2 | 7/2013 | Hook et al. |
| 8,735,327 B2 | 5/2014 | Macula |
| 8,769,689 B2 | 7/2014 | Hoglund |
| 8,806,127 B2 | 8/2014 | Brownell et al. |
| 8,856,940 B2 | 10/2014 | Kencl et al. |
| 8,937,564 B2 | 1/2015 | Aloni et al. |
| 9,061,494 B2 | 6/2015 | Rogers et al. |
| 9,062,218 B2 | 6/2015 | Oshima et al. |
| 9,187,777 B2 | 11/2015 | Jacobson et al. |
| 9,266,370 B2 | 2/2016 | Jung et al. |
| 9,317,664 B2 | 4/2016 | Ahuja et al. |
| 9,384,320 B2 | 7/2016 | Church |
| 9,403,180 B2 | 8/2016 | Ha et al. |
| 9,487,002 B2 | 11/2016 | Rogers et al. |
| 9,616,661 B2 | 4/2017 | Pierik et al. |
| 9,679,030 B2 | 6/2017 | Hatami-Hanza |
| 9,684,678 B2 | 6/2017 | Hatami-Hanza |
| 9,774,351 B2 | 9/2017 | Huetter et al. |
| 9,830,553 B2 | 11/2017 | Chen et al. |
| 9,904,734 B2 | 2/2018 | Murrah et al. |
| 9,928,869 B2 | 3/2018 | Church |
| 9,996,778 B2 | 6/2018 | Church |

(Continued)

FOREIGN PATENT DOCUMENTS

| | | |
|---|---|---|
| EP | 1512749 A2 | 3/2005 |
| EP | 2329425 A1 | 6/2011 |
| EP | 2856375 A2 | 4/2015 |
| EP | 3346404 A1 | 7/2018 |
| JP | 2009244996 | 10/2009 |

(Continued)

OTHER PUBLICATIONS

De Silva, et al., "New Trends of Digital Data Storage in DNA", BioMed Research International, vol. 2016, Article ID 8072463, 14 pages (Sep. 5, 2016) p. 14.
Extended European Search Report issued in EP Application No. 17872172.6 dated Oct. 27, 2020.
Bonnet et al., "Rewritable digital data storage in live cells via engineered control of recombination directionality," Proceeding of the National Academy of Sciences, vol. 109(23): 8884-8889 (2012).

(Continued)

*Primary Examiner* — Narayan K Bhat
(74) *Attorney, Agent, or Firm* — McDermott Will & Emery LLP

(57) ABSTRACT

Methods and systems for security, authentication, tagging, and tracking using nucleic acid (e.g., deoxyribonucleic acid) molecules encoding information. Unique nucleic acid molecules are efficiently produced from pre-fabricated fragments to quickly produce libraries of nucleic acid molecules encoding encrypted or randomized information. Physical objects or artifacts can be tagged with libraries to authenticate the objects, grant access to secured assets or locations, or track the objects or entities. Chemical methods can be applied to verify authenticity, decrypt, or decode information stored in the libraries.

30 Claims, 19 Drawing Sheets

(56) References Cited

U.S. PATENT DOCUMENTS

| | | |
|---|---|---|
| 10,020,826 B2 | 7/2018 | Gladwin et al. |
| 10,027,347 B2 | 7/2018 | Le Scouarnec et al. |
| 10,047,235 B2 | 8/2018 | Wilsher et al. |
| 10,050,959 B2 | 8/2018 | Soon-Shiong et al. |
| 10,287,573 B2 | 5/2019 | Macula |
| 10,289,801 B2 | 5/2019 | Church |
| 10,370,246 B1 | 8/2019 | Milenkovic et al. |
| 10,387,301 B2 | 8/2019 | Goldman et al. |
| 10,417,457 B2 | 9/2019 | Peck |
| 10,423,341 B1 | 9/2019 | Kermani |
| 10,438,662 B2 | 10/2019 | Predki |
| 10,460,220 B2 | 10/2019 | Church |
| 10,566,077 B1 | 2/2020 | Milenkovic et al. |
| 10,640,822 B2 | 5/2020 | Predki et al. |
| 10,650,312 B2 | 5/2020 | Roquet et al. |
| 10,669,558 B2 | 6/2020 | Ganjam |
| 10,742,233 B2 | 8/2020 | Erlich |
| 10,754,994 B2 | 8/2020 | Peck |
| 10,774,379 B2 | 9/2020 | Chen et al. |
| 10,787,699 B2 | 9/2020 | Chen et al. |
| 10,793,897 B2 | 10/2020 | Chen et al. |
| 10,818,378 B2 | 10/2020 | Hutchison, III et al. |
| 10,838,939 B2 | 11/2020 | Walder et al. |
| 10,839,295 B2 | 11/2020 | Shen et al. |
| 10,853,244 B2 | 12/2020 | Petti et al. |
| 10,883,140 B2 | 1/2021 | Church et al. |
| 10,902,939 B2 | 1/2021 | Merriman et al. |
| 10,917,109 B1 | 2/2021 | Dimopoulou et al. |
| 10,920,274 B2 | 2/2021 | Hogan et al. |
| 10,929,039 B2 | 2/2021 | Kwon et al. |
| 10,936,953 B2 | 3/2021 | Peck et al. |
| 10,956,806 B2 | 3/2021 | Masuda et al. |
| 2003/0116630 A1 | 6/2003 | Carey et al. |
| 2004/0244623 A1 | 12/2004 | Hayashizaki |
| 2005/0019760 A1 | 1/2005 | Southern |
| 2005/0166782 A2 | 8/2005 | Hayashizaki |
| 2005/0243618 A1 | 11/2005 | Boland et al. |
| 2006/0263534 A1 | 11/2006 | Laurent et al. |
| 2008/0252679 A1 | 10/2008 | Pierik et al. |
| 2008/0269152 A1 | 10/2008 | Verdine et al. |
| 2008/0303870 A1 | 12/2008 | Verbeek et al. |
| 2008/0309701 A1 | 12/2008 | Pierik et al. |
| 2009/0023607 A1 | 1/2009 | Rozhok et al. |
| 2009/0033690 A1 | 2/2009 | Pierik et al. |
| 2009/0062129 A1 | 3/2009 | McKernan et al. |
| 2009/0253141 A1 | 10/2009 | Quake |
| 2010/0029490 A1 | 2/2010 | Pierik et al. |
| 2010/0056381 A1 | 3/2010 | Kurt et al. |
| 2011/0195850 A1 | 8/2011 | Rozhok et al. |
| 2011/0312779 A1 | 12/2011 | Silverbrook et al. |
| 2011/0312782 A1 | 12/2011 | Azimi et al. |
| 2011/0312847 A1 | 12/2011 | Silverbrook et al. |
| 2011/0312851 A1 | 12/2011 | Silverbrook et al. |
| 2011/0312853 A1 | 12/2011 | Azimi et al. |
| 2011/0312855 A1 | 12/2011 | Silverbrook et al. |
| 2011/0312856 A1 | 12/2011 | Silverbrook et al. |
| 2012/0164396 A1 | 6/2012 | Mirkin et al. |
| 2012/0329561 A1 | 12/2012 | Evans et al. |
| 2013/0231254 A1 | 9/2013 | Kawashima et al. |
| 2013/0233709 A1 | 9/2013 | Dunbar |
| 2014/0065609 A1* | 3/2014 | Hicks .................... C12Q 1/683 435/6.11 |
| 2014/0296087 A1 | 10/2014 | Verdine et al. |
| 2014/0371100 A1 | 12/2014 | Kawashima et al. |
| 2015/0083797 A1 | 3/2015 | Tran et al. |
| 2015/0261664 A1 | 9/2015 | Goldman et al. |
| 2015/0269313 A1 | 9/2015 | Church |
| 2015/0312212 A1 | 10/2015 | Holmes et al. |
| 2015/0363550 A1 | 12/2015 | Green, Jr. et al. |
| 2016/0007893 A1 | 1/2016 | Roberts |
| 2016/0051985 A1 | 2/2016 | Knight et al. |
| 2016/0168579 A1 | 6/2016 | Hutchison et al. |
| 2016/0258939 A1 | 9/2016 | Morin |
| 2016/0304948 A1 | 10/2016 | Lee et al. |
| 2016/0371434 A1 | 12/2016 | Strauss et al. |
| 2017/0017436 A1 | 1/2017 | Church |
| 2017/0021611 A1 | 1/2017 | Jung et al. |
| 2017/0081716 A1 | 3/2017 | Peck |
| 2017/0093851 A1 | 3/2017 | Allen |
| 2017/0109229 A1 | 4/2017 | Huetter et al. |
| 2017/0136452 A1 | 5/2017 | Niles et al. |
| 2017/0140095 A1 | 5/2017 | Kim |
| 2017/0218228 A1 | 8/2017 | Jose et al. |
| 2017/0363953 A1 | 12/2017 | Steinhart et al. |
| 2018/0068060 A1 | 3/2018 | Ceze et al. |
| 2018/0086781 A1 | 3/2018 | Liss |
| 2018/0101487 A1 | 4/2018 | Peck |
| 2018/0121478 A1 | 5/2018 | Walder et al. |
| 2018/0137418 A1 | 5/2018 | Roquet et al. |
| 2018/0173710 A1 | 6/2018 | Maftuleac et al. |
| 2018/0173738 A1 | 6/2018 | Lopez-Ortiz et al. |
| 2018/0253563 A1 | 9/2018 | Peck et al. |
| 2019/0020651 A1 | 1/2019 | Soon-Shiong et al. |
| 2019/0136307 A1 | 5/2019 | Predki |
| 2019/0142882 A1 | 5/2019 | Shepherd et al. |
| 2019/0271032 A1 | 9/2019 | Owen |
| 2019/0325040 A1* | 10/2019 | Sagi .................... G06F 16/137 |
| 2019/0344239 A1 | 11/2019 | Efcavitch et al. |
| 2019/0351673 A1 | 11/2019 | Roquet et al. |
| 2019/0355442 A1 | 11/2019 | Merriman |
| 2020/0185057 A1 | 6/2020 | Leake et al. |
| 2020/0193301 A1 | 6/2020 | Roquet et al. |
| 2021/0010065 A1 | 1/2021 | Salk et al. |

FOREIGN PATENT DOCUMENTS

| | | |
|---|---|---|
| WO | WO-03025123 A2 | 3/2003 |
| WO | WO-2004009844 | 1/2004 |
| WO | WO-2012058638 A2 | 5/2012 |
| WO | WO-2014014991 A2 | 1/2014 |
| WO | WO-2015144858 A1 | 10/2015 |
| WO | WO-2016015701 A1 | 2/2016 |
| WO | WO2016/032562 * | 3/2016 |
| WO | WO-2016032562 A1 | 3/2016 |
| WO | WO-2016059610 A1 | 4/2016 |
| WO | WO-2016081834 A2 | 5/2016 |
| WO | WO-2016164779 A1 | 10/2016 |
| WO | WO-2016182814 A2 | 11/2016 |
| WO | WO-2017151195 A1 | 9/2017 |
| WO | WO-2017189914 A1 | 11/2017 |
| WO | WO-2017190297 A1 | 11/2017 |
| WO | WO-2017192633 A1 | 11/2017 |
| WO | WO-2018017131 A1 | 1/2018 |
| WO | WO-2018049272 A1 | 3/2018 |
| WO | WO-2018094108 A1 | 5/2018 |
| WO | WO-2018132457 A1 | 7/2018 |
| WO | WO-2018148260 A1 | 8/2018 |
| WO | WO-2018148458 A1 | 8/2018 |
| WO | WO-2018213856 A2 | 11/2018 |
| WO | WO-2019046768 A1 | 3/2019 |
| WO | WO-2019081145 A1 | 5/2019 |
| WO | WO-2019178551 A1 | 9/2019 |
| WO | WO-2019246434 A1 | 12/2019 |
| WO | WO-2020028912 A2 | 6/2020 |
| WO | WO-2020128517 A1 | 6/2020 |
| WO | WO-2020132935 A1 | 7/2020 |

OTHER PUBLICATIONS

Bornholt et al., "A DNA-Based Archival Storage System," International Conference on Architectural Support for Programming Languages and Operating Systems (ASPLOS), Apr. 2-6, 2016, Atlanta, GA, 637-649.

Buschmann, et al., "Levenshtein Error-Correcting Barcodes for Multiplexed DNA Sequencing", BMC Bioinformatics, vol. 14, No. 1., pp. 1-10 (2013).

Bystrykh, et al., "Generalized DNA Barcode Design Based on Hamming Codes", PLOS ONE, vol. 7, No. 5, pp. 1-8, (May 2012).

Casini, A. "Advanced DNA assembly strategies and standards for synthetic biology," Thesis, Department of Life Sciences, Imperial College London: 1-178 (2014).

(56) References Cited

OTHER PUBLICATIONS

Clarke, et al., "Continuous base identification for single-molecule nanopore DNA sequencing", Nature Nanotechnology, vol. 4, No. 4, pp. 265-270, Feb. 22, 2009.
Deorowicz et al., "Data compression for sequencing data," Algorithms for Molecular Biology, vol. 8(25): 1-13 (2013).
Engler et al., "A One Pot, One Step, Precision Cloning Method with High Throughput Capability," PLoS ONE, vol. 3(11): E3647 (2008) printed as pp. 1-7.
Engler et al., "Chapter 12: Combinatorial DNA Assembly Using Golden Gate Cloning," Karen M. Polizzi and Cleo Kontoravadi (eds.), Synthetic Biology, Methods in Molecular Biology, vol. 1073, Springer Science+Business Media, New York: 141-156 (2013).
Fogg et al., "New Applications for Phage Integrases," Journal of Molecular Biology, vol. 426(15): 2703-2716 (2014).
Goldman et al., "Towards practical, high-capacity, low-maintenance information storage in synthesized DNA," Nature, vol. 494: 77-80 (2013).
Kivioja et al., "Counting absolute numbers of molecules using unique molecular identifiers," Nature Methods, vol. 9(1): 72-74 (2011), including pp. 1-2 of Online Methods, and pp. 1-14 of Supplementary Information.
Lee, et al., "Enzymatic DNA synthesis for digital information storage", bioRxiv, XP055603868, DOI: 10.1101/348987 Retrieved from the Internet: URL:https://www.biorxiv.org/content/biorxiv/early/2018/06/16/348987.full.pdf [retrieved on Nov. 20, 2019] abstract, pp. 5, 8ff (Jun. 16, 2018).
Leier et al., "Cryptography with DNA binary strands," Biosystems, vol. 57: 13-22 (2000).
Navarro, et al., "Compressed Full-Text Indexes", ACM Computing Surveys, ACM, New York, NY, vol. 39, No. 1 Apr. 12, 2007.
Organick, et al., "Random access in large-scale DNA data storage", Nature Biotechnology, vol. 36, No. 3, pp. 242-248, (Mar. 1, 2018).
PCT/US2017/062098 International Search Report and Written Opinion, dated Mar. 14, 2018.
PCT/US2017/062106 International Search Report and Written Opinion, dated Feb. 22, 2018.
PCT/US2019/022596 International Search Report and Written Opinion, dated Jun. 28, 2019.
PCT/US2019/032756 International Search Report and Written Opinion, dated Sep. 4, 2019.
PCT/US2020/032384 International Search Report and Written Opinion, dated, Jul. 30, 2020.
Quetier et al., "The CRISPR-Cas9 technology: Closer to the ultimate toolkit for targeted genome editing," Plant Science, vol. 242: 65-76 (2015).
Roquet et al., "Synthetic recombinase-based state machines in living cells," Science, vol. 353(6297): 363, aad8559-1-aad8559-13 (2016).
Sands, B. and Brent, R., "Overview of Post Cohen-Boyer Methods for Single Segment Cloning and for Multisegment DNA Assembly," Current Protocols in Molecular Biology, vol. 113: 3.26.1-3.26-20 (2016).
Sorek et al., "CRISPR-Mediated Adaptive Immune Systems in Bacteria and Archaea," Annual Review of Biochemistry, vol. 82: 237-266 (2013).
Sun et al., "Recent advances in targeted genome engineering in mammalian systems," Biotechnology Journal, vol. 7: 1074-1087 (2012).
Tulpan, et al., "HyDEn: A Hybrid Steganocryptographic Approach for Data Encryption Using Randomized Error Correcting DNA Codes,", Biomed Research International, vol. 32, No. 4839, pp. 1-11, (2013).
Yang et al., "Permanent genetic memory with >1-byte capacity," Nature Methods, vol. 11(12): 1261-1266 (2014) including pp. 1-3 of Online Methods, and pp. 1-30 of Supplementary Figures and Text.
Yazdi et al., "A Rewritable, Random-Access DNA-Based Storage System," Scientific Reports, vol. 5(14138): 1-10 (2015), including pp. 1-19 of Supplementary Information.

Yazdi et al., "DNA-based storage: Trends and Methods," IEEE Transactions on Molecular, Biological, and Multi-Scale Communications, vol. 1(3): 230-248 (2015).
Yazdi, et al., "Portable and Error-Free DNA-Based Data Storage", bioRxiv preprint doi: https://doi.org/10.1101/079442 (2016).
Yim et al., "The essential component in DNA-based information storage system: robust error-tolerating module," Frontiers in Bioengineering and Biotechnology, vol. 2, Article 49: 1-5 (2014).
Zhu et al., "High-throughput DNA sequence data compression," Briefings in Bioinformatics, 16(1): 1-15 (2015).
PCT/US2019/045160 International Search Report and Written Opinion dated, Jan. 30, 2020.
Patrick, et al., DNA Assembly in 3D Printed Fluidics, PLOS One, 10(12): e014636 18 pages (2015).
Arppe, R., et al., "Physical Unclonable Functions Generated Through Chemical Methods for Anti-Counterfeiting", Nature Reviews Chemistry, 1, 31 (2017).
Chandrasekaran, A. R., et al., "Addressable Configurations of DNA Nanostructures for Rewritable Memory", Nucleic Acids Res., 45, 19, pp. 11459-11465. (2017).
Church, G. M., et al., "Next-Generation Digital Information Storage in DNA", Science 2012, 337 (6102), 1628 (2012).
Clelland, C. T., et al., "Hiding Messages in DNA microdots", Nature, 399, 533. (1999).
Erlich, Y., et al., "DNA Fountain Enables a Robust and Efficient Storage Architecture", Science, 355 (6328), 950-954 (2017).
Gehani, A., et al., DNA-based Cryptography. In Aspects of Molecular Computing; Jonoska, N., Păun, G., Rozenberg, G., Eds.; Springer: Berlin, Heidelberg, 2004; pp. 167-188 (2004).
Goldman, N., et al., "Toward Practical High-Capacity Low-Maintenance Storage of Digital Information in Synthesised DNA", Nature, 494 (7435), 77-80 (2013).
Grass, R. N., et al., "Robust Chemical Preservation of Digital Information on DNA in Silica with Error-Correcting Codes", Angew. Chem., Int. Ed. 2015, 54 (8), 2552-2555 (2015).
Halvorsen, K., et al., "Binary DNA Nanostructures for Data Encryption", PLoS One 2012, 7 (9), No. e44212. (2012).
Holden, et al., "Encrypted Oligonucleotide Arrays for Molecular Authentication", American Chemical Society, 6 pages (Jul. 5, 2019).
PCT/US2020/055351 International Search Report and Written Opinion dated, Mar. 31, 2021.
Shoshani, S., et al., "A Molecular Cryptosystem for Images by DNA Computing", Angew. Chem., Int. Ed., 51 (12), 2883-2887 (2012).
Issued U.S. Pat. No. 10,650,312 (U.S. Appl. No. 15/850,112), filed Dec. 21, 2017.
Pending U.S. Appl. No. 16/847,064, filed Apr. 13, 2020.
Pending U.S. Appl. No. 17/007,946, filed Aug. 31, 2020.
Pending U.S. Appl. No. 16/461,774, filed May 16, 2019.
Pending U.S. Appl. No. 17/012,909, filed Sep. 4, 2020.
Pending U.S. Appl. No. 16/414,758, filed May 16, 2019.
Pending U.S. Appl. No. 17/206,803, filed Mar. 19, 2021.
Pending U.S. Appl. No. 16/532,077, filed Aug. 5, 2019.
Pending U.S. Appl. No. 17/206,886, filed Mar. 19, 2021.
Pending U.S. Appl. No. 16/872,129, filed May 11, 2020.
Craig, et al., "Ordering of Cosmid Clones covering the Herpes Simplex Virus Type 1 (HSV-1) genome: a test case for fingerprinting by hybridisation", Nucleic Acids Research, vol. 18, pp. 2653-2660 (1990).
Lee et al, DNA detection using commercial mobile phones, Biosensors and Bioelectronics, 2011, 26, 4349-4354 (Year: 2011).
Burks et al., "The GenBank Nucleic Acid Sequence Database," Cabios Review, vol. 1(4): 225-233 (1985).
PCT/US2021/031865 International Search Report and Written Opinion dated, Aug. 13, 2021.
PCT/US2021/049289 International Search Report and Written Opinion dated, Nov. 18, 2021.
PCT/US2022/020949 International Search Report and Written Opinion dated, Jun. 23, 2022.
Staden, R., "Nucleic Acids Research—Sequence Data Handling by Computer," vol. 4(11): 4037-4052 (1977).

* cited by examiner $C_{xy}$ is the yth component in layer x. For a starting library with M layers, each with N components, the identifiers would have the following architecture:

where a, b, c represent elements in the set {1, 2, ..., N}

NUCLEIC ACID SECURITY AND AUTHENTICATION

CROSS-REFERENCE TO RELATED APPLICATIONS

This application claims priority to and the benefit of U.S. Provisional Patent Application No. 62/914,086, filed on Oct. 11, 2019, and entitled "DNA STORAGE FOR SECURITY AND AUTHENTICATION", the entire contents of the which is incorporated herein by reference.

BACKGROUND

Nucleic acid digital data storage is a stable approach for encoding and storing information for long periods of time, with data stored at higher densities than magnetic tape or hard drive storage systems. Additionally, digital data stored in nucleic acid molecules that are stored in cold and dry conditions can be retrieved as long as 60,000 years later or longer.

Current methods rely on encoding the digital information (e.g., binary code) into base-by-base nucleic acids sequences, such that the base to base relationship in the sequence directly translates into the digital information (e.g., binary code). Sequencing of digital data stored in base-by-base sequences that can be read into bit-streams or bytes of digitally encoded information can be error prone and costly to encode since the cost of de novo base-by-base nucleic acid synthesis can be expensive. Opportunities for new methods of performing nucleic acid digital data storage may provide approaches for encoding and retrieving data that are less costly and easier to commercially implement.

SUMMARY

Provided herein are methods and systems for encoding digital information in nucleic acid (e.g., deoxyribonucleic acid, DNA) molecules without base-by-base synthesis, by encoding bit-value information in the presence or absence of unique nucleic acid sequences within a pool, comprising specifying each bit location in a bit-stream with a unique nucleic sequence and specifying the bit value at that location by the presence or absence of the corresponding unique nucleic acid sequence in the pool. These encoded nucleic acid molecules are particularly useful for encoding sensitive information or tagging artifacts with information in very small chemical quantities. By being associating an artifact with an amount of nucleic acid molecules encoding information, an artifact can be uniquely tagged in a way that is not readily apparent to outside users, such that the artifact can be used for secure authentication or tracking the origin of the artifact.

In an aspect, provided herein is a method for tagging a fluid for tracking or authentication. The method comprises obtaining a library of nucleic acid molecules representing digital information, and combining the fluid with a tag comprising the library of nucleic acid molecules to obtain a tagged fluid for tracking or authentication. Tagging fluids can be advantageous for certifying the authenticity of the fluid, like a valuable fuel or pharmaceutical, because the library can be designed to uniquely identify the fluid, its origin, its manufacture date, or any other characteristic of the fluid.

In some implementations, the method further comprises sampling the tagged fluid to obtain a sample containing at least a part of the library of nucleic acid molecules. Sampling may involve swabbing or drawing a volume from the tag or the tagged fluid. In some implementations, the method further involves sequencing nucleic acid molecules of the sample to obtain a sequencing readout. The sequencing readout may be compared to a reference sequence to determine a presence of a matching sequence. Thus, the information encoded by the library may be determined, and the fluid may be authenticated or identified.

The fluid may be any one of an oil, an ink, a compressed gas, or a drug. In some implementations, the method further comprises measuring a concentration of the tag in the tagged fluid to determine an amount of dilution. This step is useful for determining if the fluid was tampered with.

In some implementations, the tag comprises a molecular barcode specific to the tag. The information may comprise a message or a currency value. The information may comprise at least a kilobit of information. In some implementations, the method further comprises accessing the tagged fluid, thereby causing the tag in the tagged fluid to decay. In some implementations, the tag is part of a two-factor authentication system.

In some implementations, the library is randomly generated. In some implementations, the library is generated by selecting a subset of nucleic acid molecules from a pool of nucleic acid molecules. In some implementations, the information comprises a plurality of symbols, and each symbol is represented by a distinct sequence of a nucleic acid molecule of the library. In some implementations, the information is represented by the library of nucleic acid molecules via an encoding scheme wherein the information is mapped to a plurality of symbols having one of two possible symbol values, wherein a symbol of the plurality of symbols is represented by presence of a distinct nucleic acid molecule in the library if the symbol has a first symbol value of the two possible symbol values, and wherein the symbol is represented by absence of the distinct nucleic acid molecule if the symbol has a second symbol value of the two possible symbol values.

In another aspect, provided herein is a method for preparing a library of nucleic acid molecules for use in security and authentication. The method involves obtaining the library of nucleic acid molecules representing a security token, and applying a chemical operation to the library representing the security token to obtain a hashed library of nucleic acid molecules representing a hashed token. This method is advantageous over conventional methods by air-gapping the value of the security token by hashing the token prior to reading the library of nucleic acid molecules, such that the sequences of the pre-hashing library are never revealed.

In some implementations, the chemical operation effects one or more Boolean functions on the security token. For example, the one or more Boolean functions apply a hash function to the security token to obtain the hashed token represented by the hashed library. In some implementations, the hashed library is a subset of the library.

In some implementations, the method further comprises sequencing at least a portion of the nucleic acid molecules of the hashed library to obtain a sequencing readout. The sequencing readout may be compared to a database or look-up table to determine a presence or absence of a matching sequence. The method may further involve granting or denying access to a secured asset or location based on the determined presence or absence of the matching sequence, respectively. For example, sequencing comprises any one of high-throughput sequencing, shotgun sequencing, or nanopore sequencing.

In some implementations, the method further comprises applying an additional chemical operation to the hashed library to produce an output molecule if the hashed token matches a reference sequence, and determining a presence or absence of the output molecule via an assay. For example, the assay is one of polymerase chain reaction (PCR), real-time PCR, reverse transcription PCR (RT-PCR), fluorimetry, and gel electrophoresis. The output molecule may be a distinct nucleic acid molecule of the hashed library. In some implementations, the method further involves granting or denying access to a secured asset or location based on the presence of the output molecule. This implementation of validating the hashed token chemically to produce an output molecule is advantageous in that it obviates the need for sequencing of the hashed library; rather, the hashed library undergoes further chemical operations that may be cheaper or faster than sequencing in order to determine the authenticity of the security token.

In some implementations, the library comprises a unique molecular barcode. In some implementations, the security token comprises a randomly generated key. In some implementations, the security token is part of a two-factor authentication system. In some implementations, the library is collocated with an artifact, and wherein the security token is unique to the artifact. For example, the artifact is a fluid. The fluid may be any one of an oil, an ink, a compressed gas, or a drug. In some implementations, the method further involves measuring a concentration of the library in the fluid to determine an amount of dilution. As another example, the artifact is an organism or a document. In some implementations, the library is contained in any one of a well, a droplet, a spot, a sealed container, a gel, a suspension, or a solid matrix. In some implementations, the library is lyophilized.

In some implementations, the library is generated by selecting a subset of nucleic acid molecules from a pool of nucleic acid molecules. In some implementations, the security token comprises a plurality of symbols, and each symbol is represented by a distinct sequence of a nucleic acid molecule of the library. In some implementations, the library is randomly generated. In some implementations, the security token is represented by the library of nucleic acid molecules via an encoding scheme wherein the security token is mapped to a plurality of symbols having one of two possible symbol values, wherein a symbol of the plurality of symbols is represented by presence of a distinct nucleic acid molecule in the library if the symbol has a first symbol value of the two possible symbol values, and wherein the symbol is represented by absence of the distinct nucleic acid molecule if the symbol has a second symbol value of the two possible symbol values. In some implementations, the security token comprises at least a kilobit of information. In some implementations, the security token is unique to a user.

Additional aspects and advantages of the present disclosure will become readily apparent to those skilled in this art from the following detailed description, wherein only illustrative implementations of the present disclosure are shown and described. As will be realized, the present disclosure is capable of other and different implementations, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative implementations, in which the principles of the invention are utilized, and the accompanying drawings (also "Figure" and "FIG." herein), of which:

FIG. 2A illustrates combining a rank object (or address object) with a byte-value object (or data object) to create an identifier, according to an illustrative implementation; FIG. 2B illustrates an implementation of the data at address method wherein the rank objects and byte-value objects are themselves combinatorial concatenations of other objects, according to an illustrative implementation;

FIG. 3A illustrates encoding digital information using a rank object as an identifier, according to an illustrative implementation;

FIG. 3B illustrates an implementation of the encoding method wherein the address objects are themselves combinatorial concatenations of other objects, according to an illustrative implementation;

FIG. 6A illustrates the architecture of identifiers constructed using the product scheme, according to an illustrative implementation; FIG. 6B illustrates an example of the combinatorial space of identifiers that may be constructed using the product scheme, according to an illustrative implementation;

FIG. 7A shows example methods for using polymerase chain reaction, affinity tagged probes, and degradation targeting probes to access identifiers containing a specified component, according to an illustrative implementation;

FIG. 7B shows example methods for using polymerase chain reaction to perform 'OR' or 'AND' operations to access identifiers containing multiple specified components, according to an illustrative implementation; FIG. 7C shows example methods for using affinity tags to perform 'OR' or 'AND' operations to access identifiers containing multiple specified components, according to an illustrative implementation;

FIG. 17A shows an example of encoding, writing, and reading 5,856 bits of data, according to an illustrative implementation; FIG. 17B shows an example of encoding, writing, and reading 62,824 bits of data, according to an illustrative implementation.

DETAILED DESCRIPTION

Figure 1:
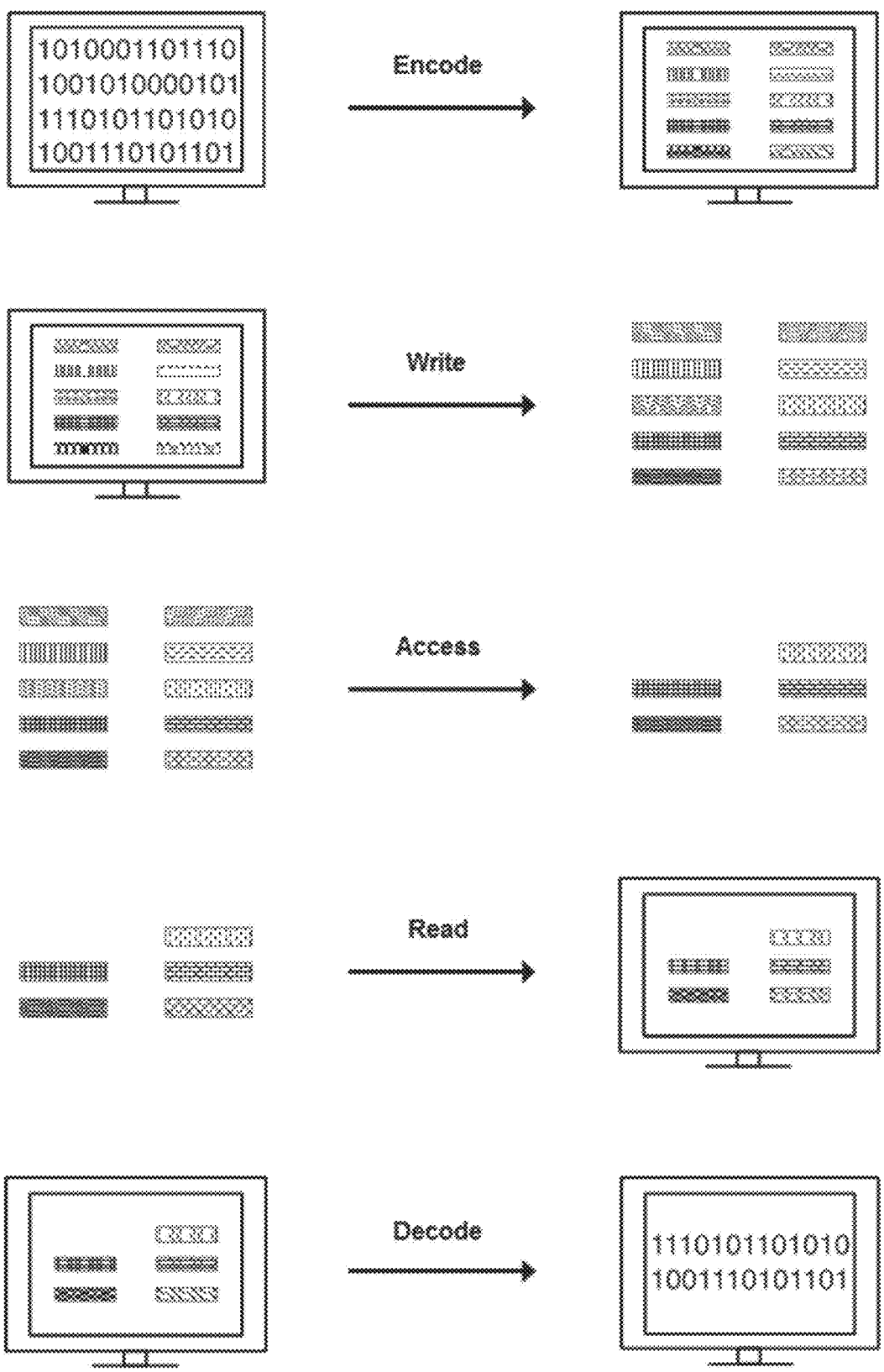
FIG. 1 schematically illustrates an overview of a process for encoding, writing, accessing, querying, reading, and decoding digital information stored in nucleic acid sequences, according to an illustrative implementation.

While various implementations of the invention have been shown and described herein, it will be obvious to those skilled in the art that such implementations are provided by way of example only. Numerous variations, changes, and substitutions may occur to those skilled in the art without departing from the invention. It should be understood that various alternatives to the implementations of the invention described herein may be employed.

The term "symbol," as used herein, generally refers to a representation of a unit of digital information. Digital information may be divided or translated into a string of symbols. In an example, a symbol may be a bit and the bit may have a value of '0' or '1'.

The term "distinct," or "unique," as used herein, generally refers to an object that is distinguishable from other objects in a group. For example, a distinct, or unique, nucleic acid sequence may be a nucleic acid sequence that does not have the same sequence as any other nucleic acid sequence. A distinct, or unique, nucleic acid molecule may not have the same sequence as any other nucleic acid molecule. The distinct, or unique, nucleic acid sequence or molecule may share regions of similarity with another nucleic acid sequence or molecule.

The term "component," as used herein, generally refers to a nucleic acid sequence. A component may be a distinct nucleic acid sequence. A component may be concatenated or assembled with one or more other components to generate other nucleic acid sequence or molecules.

The term "layer," as used herein, generally refers to group or pool of components. Each layer may comprise a set of distinct components such that the components in one layer are different from the components in another layer. Components from one or more layers may be assembled to generate one or more identifiers.

The term "identifier," as used herein, generally refers to a nucleic acid molecule or a nucleic acid sequence that represents the position and value of a bit-string within a larger bit-string. More generally, an identifier may refer to any object that represents or corresponds to a symbol in a string of symbols. In some implementations, identifiers may comprise one or multiple concatenated components.

The term "combinatorial space," as used herein generally refers to the set of all possible distinct identifiers that may be generated from a starting set of objects, such as components, and a permissible set of rules for how to modify those objects to form identifiers. The size of a combinatorial space of identifiers made by assembling or concatenating components may depend on the number of layers of components, the number of components in each layer, and the particular assembly method used to generate the identifiers.

The term "identifier rank," as used herein generally refers to a relation that defines the order of identifiers in a set.

The term "identifier library," as used herein generally refers to a collection of identifiers corresponding to the symbols in a symbol string representing digital information. In some implementations, the absence of a given identifier in the identifier library may indicate a symbol value at a particular position. One or more identifier libraries may be combined in a pool, group, or set of identifiers. Each identifier library may include a unique barcode that identifies the identifier library.

The term "nucleic acid," as used herein, general refers to deoxyribonucleic acid (DNA), ribonucleic acid (RNA), or a variant thereof. A nucleic acid may include one or more subunits selected from adenosine (A), cytosine (C), guanine (G), thymine (T), and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that may be specific to one of more complementary A, C, G, T, or U, or complementary to a purine (i.e., A or G, or variant thereof) or pyrimidine (i.e., C, T, or U, or variant thereof). In some examples, a nucleic acid may be single-stranded or double stranded, in some cases, a nucleic acid is circular.

The terms "nucleic acid molecule" or "nucleic acid sequence," as used herein, generally refer to a polymeric form of nucleotides, or polynucleotide, that may have various lengths, either deoxyribonucleotides (DNA) or ribonucleotides (RNA), or analogs thereof. The term "nucleic acid sequence" may refer to the alphabetical representation of a polynucleotide; alternatively, the term may be applied to the physical polynucleotide itself. This alphabetical representation can be input into databases in a computer having a central processing unit and used for mapping nucleic acid sequences or nucleic acid molecules to symbols, or bits, encoding digital information. Nucleic acid sequences or oligonucleotides may include one or more non-standard nucleotide(s), nucleotide analog(s) and/or modified nucleotides.

An "oligonucleotide", as used herein, generally refers to a single-stranded nucleic acid sequence, and is typically composed of a specific sequence of four nucleotide bases: adenine (A); cytosine (C); guanine (G), and thymine (T) or uracil (U) when the polynucleotide is RNA.

Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexylacrylamide-dCTP (aha-dCTP) to allow covalent attachment of amine reactive moieties, such as N-hydroxy succinimide esters (NHS).

The term "primer," as used herein, generally refers to a strand of nucleic acid that serves as a starting point for nucleic acid synthesis, such as polymerase chain reaction (PCR). In an example, during replication of a DNA sample, an enzyme that catalyzes replication starts replication at the 3'-end of a primer attached to the DNA sample and copies the opposite strand. See Chemical Methods Section D for more information on PCR, including details about primer design.

The term "polymerase" or "polymerase enzyme," as used herein, generally refers to any enzyme capable of catalyzing a polymerase reaction. Examples of polymerases include, without limitation, a nucleic acid polymerase. The polymerase can be naturally occurring or synthesized. An example polymerase is a Φ29 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase 129 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. See Chemical Methods Section D for additional polymerases that may be used with PCR as well as for details on how polymerase characteristics may affect PCR.

The term "species", as used herein, generally refers to one or more DNA molecule(s) of the same sequence. If "species" is used in a plural sense, then it may be assumed that every species in the plurality of species has a distinct sequence, though this may sometimes be made explicit by writing "distinct species" instead of "species".

The terms "about" and "approximately" should be understood to mean within plus or minus 20% of a value which follows said terms.

Digital information, such as computer data, in the form of binary code can comprise a sequence or string of symbols. A binary code may encode or represent text or computer processor instructions using, for example, a binary number system having two binary symbols, typically 0 and 1, referred to as bits. Digital information may be represented in the form of non-binary code which can comprise a sequence of non-binary symbols. Each encoded symbol can be re-assigned to a unique bit string (or "byte"), and the unique bit string or byte can be arranged into strings of bytes or byte streams. A bit value for a given bit can be one of two symbols (e.g., 0 or 1). A byte, which can comprise a string of N bits, can have a total of $2^N$ unique byte-values. For example, a byte comprising 8 bits can produce a total of $2^8$ or 256 possible unique byte-values, and each of the 256 bytes can correspond to one of 256 possible distinct symbols, letters, or instructions which can be encoded with the bytes. Raw data (e.g., text files and computer instructions) can be represented as strings of bytes or byte streams. Zip files, or compressed data files comprising raw data can also be stored in byte streams, these files can be stored as byte streams in a compressed form, and then decompressed into raw data before being read by the computer.

Methods and systems of the present disclosure may be used to encode computer data or information in a plurality of identifiers, each of which may represent one or more bits of the original information. In some examples, methods and systems of the present disclosure encode data or information using identifiers that each represents two bits of the original information.

Previous methods for encoding digital information into nucleic acids have relied on base-by-base synthesis of the nucleic acids, which can be costly and time consuming. Alternative methods may improve the efficiency, improve the commercial viability of digital information storage by reducing the reliance on base-by-base nucleic acid synthesis for encoding digital information, and eliminate the de novo synthesis of distinct nucleic acid sequences for every new information storage request.

New methods can encode digital information (e.g., binary code) in a plurality of identifiers, or nucleic acid sequences, comprising combinatorial arrangements of components instead of relying on base-by-base or de-novo nucleic acid synthesis (e.g., phosphoramidite synthesis). As such, new strategies may produce a first set of distinct nucleic acid sequences (or components) for the first request of information storage, and can there-after re-use the same nucleic acid sequences (or components) for subsequent information storage requests. These approaches can significantly reduce the cost of DNA-based information storage by reducing the role of de-novo synthesis of nucleic acid sequences in the information-to-DNA encoding and writing process. Moreover, unlike implementations of base-by-base synthesis, such as phosphoramidite chemistry- or template-free polymerase-based nucleic acid elongation, which may use cyclical delivery of each base to each elongating nucleic acid, new methods of information-to-DNA writing using identifier construction from components are highly parallelizable processes that do not necessarily use cyclical nucleic acid elongation. Thus, new methods may increase the speed of writing digital information to DNA compared to older methods.

Described herein are methods for encoding information into nucleic acid sequences. A method for encoding information into nucleic acid sequences may comprise (a) translating the information into a string of symbols, (b) mapping the string of symbols to a plurality of identifiers, and (c) constructing an identifier library comprising at least a subset of the plurality of identifiers. An individual identifier of the plurality of identifiers may comprise one or more components. An individual component of the one or more components may comprise a nucleic acid sequence. Each symbol at each position in the string of symbols may correspond to a distinct identifier. The individual identifier may correspond to an individual symbol at an individual position in the string of symbols. Moreover, one symbol at each position in the string of symbols may correspond to the absence of an identifier. For example, in a string of binary symbols (e.g., bits) of '0's and '1's, each occurrence of '0' may correspond to the absence of an identifier.

In another aspect, the present disclosure provides methods for nucleic acid-based computer data storage. A method for nucleic acid-based computer data storage may comprise (a) receiving computer data, (b) synthesizing nucleic acid molecules comprising nucleic acid sequences encoding the computer data, and (c) storing the nucleic acid molecules having the nucleic acid sequences. The computer data may be encoded in at least a subset of nucleic acid molecules synthesized and not in a sequence of each of the nucleic acid molecules.

In another aspect, the present disclosure provides methods for writing and storing information in nucleic acid sequences. The method may comprise, (a) receiving or encoding a virtual identifier library that represents information, (b) physically constructing the identifier library, and (c) storing one or more physical copies of the identifier library in one or more separate locations. An individual identifier of the identifier library may comprise one or more components. An individual component of the one or more components may comprise a nucleic acid sequence.

In another aspect, the present disclosure provides methods for nucleic acid-based computer data storage. A method for nucleic acid-based computer data storage may comprise (a) receiving computer data, (b) synthesizing a nucleic acid molecule comprising at least one nucleic acid sequence encoding the computer data, and (c) storing the nucleic acid molecule comprising the at least one nucleic acid sequence. Synthesizing the nucleic acid molecule may be in the absence of base-by-base nucleic acid synthesis.

In another aspect, the present disclosure provides methods for writing and storing information in nucleic acid sequences. A method for writing and storing information in nucleic acid sequences may comprise, (a) receiving or encoding a virtual identifier library that represents information, (b) physically constructing the identifier library, and (c) storing one or more physical copies of the identifier library in one or more separate locations. An individual identifier of the identifier library may comprise one or more components. An individual component of the one or more components may comprise a nucleic acid sequence.

FIG. 1 illustrates an overview process for encoding information into nucleic acid sequences, writing information to the nucleic acid sequences, reading information written to nucleic acid sequences, and decoding the read information. Digital information, or data, may be translated into one or more strings of symbols. In an example, the symbols are bits and each bit may have a value of either '0' or '1'. Each symbol may be mapped, or encoded, to an object (e.g., identifier) representing that symbol. Each symbol may be represented by a distinct identifier. The distinct identifier may be a nucleic acid molecule made up of components. The components may be nucleic acid sequences. The digital information may be written into nucleic acid sequences by generating an identifier library corresponding to the information. The identifier library may be physically generated by physically constructing the identifiers that correspond to each symbol of the digital information. All or any portion of the digital information may be accessed at a time. In an example, a subset of identifiers is accessed from an identifier library. The subset of identifiers may be read by sequencing and identifying the identifiers. The identified identifiers may be associated with their corresponding symbol to decode the digital data.

A method for encoding and reading information using the approach of FIG. 1 can, for example, include receiving a bit stream and mapping each one-bit (bit with bit-value of '1') in the bit stream to a distinct nucleic acid identifier using an identifier rank or a nucleic acid index. Constructing a nucleic acid sample pool, or identifier library, comprising copies of the identifiers that correspond to bit values of 1 (and excluding identifiers for bit values of 0). Reading the sample can comprise using molecular biology methods (e.g., sequencing, hybridization, PCR, etc), determining which identifiers are represented in the identifier library, and assigning bit-values of '1' to the bits corresponding to those identifiers and bit-values of '0' elsewhere (again referring to the identifier rank to identify the bits in the original bit-stream that each identifier corresponds to), thus decoding the information into the original encoded bit stream.

Encoding a string of N distinct bits, can use an equivalent number of unique nucleic acid sequences as possible identifiers. This approach to information encoding may use de-novo synthesis of identifiers (e.g., nucleic acid molecules) for each new item of information (string of N bits) to store. In other instances, the cost of newly synthesizing identifiers (equivalent in number to or less than N) for each new item of information to store can be reduced by the one-time de-novo synthesis and subsequent maintenance of all possible identifiers, such that encoding new items of information may involve mechanically selecting and mixing together pre-synthesized (or pre-fabricated) identifiers to form an identifier library. In other instances, both the cost of (1) de-novo synthesis of up to N identifiers for each new item of information to store or (2) maintaining and selecting from N possible identifiers for each new item of information to store, or any combination thereof, may be reduced by synthesizing and maintaining a number (less than N, and in some cases much less than N) of nucleic acid sequences and then modifying these sequences through enzymatic reactions to generate up to N identifiers for each new item of information to store.

The identifiers may be rationally designed and selected for ease of read, write, access, copy, and deletion operations. The identifiers may be designed and selected to minimize write errors, mutations, degradation, and read errors. See Chemical Methods Section H on the rational design of DNA sequences that comprise synthetic nucleic acid libraries (such as identifier libraries).

Figure 2A:
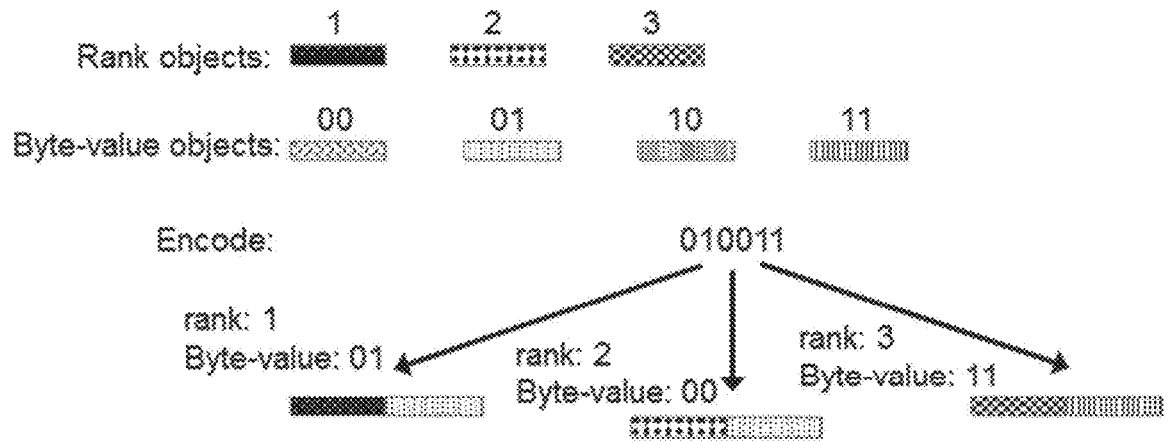
FIGS. 2A and 2B schematically illustrate an example method of encoding digital data, referred to as "data at address", using objects or identifiers (e.g., nucleic acid molecules)
Figure 2B:
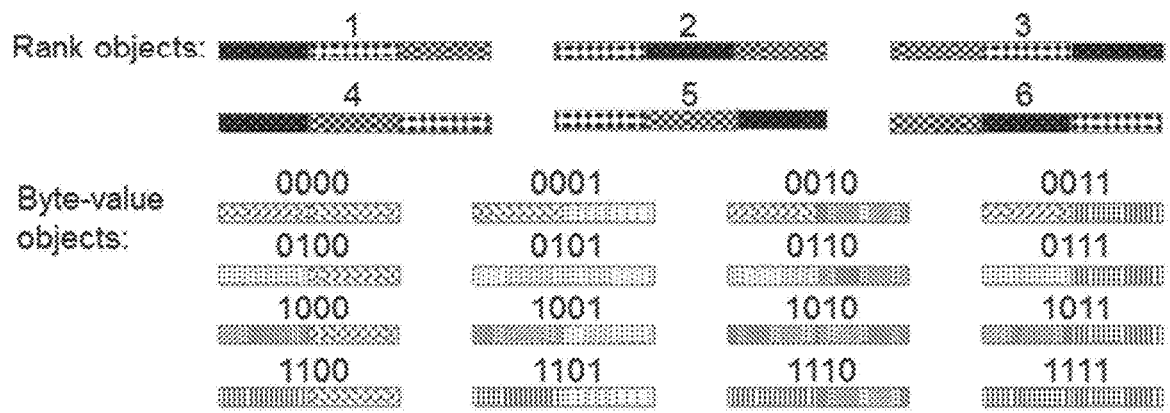

FIGS. 2A and 2B schematically illustrate an example method, referred to as "data at address", of encoding digital data in objects or identifiers (e.g., nucleic acid molecules). FIG. 2A illustrates encoding a bit stream into an identifier library wherein the individual identifiers are constructed by concatenating or assembling a single component that specifies an identifier rank with a single component that specifies a byte-value. In general, the data at address method uses identifiers that encode information modularly by comprising two objects: one object, the "byte-value object" (or "data object"), that identifies a byte-value and one object, the "rank object" (or "address object"), that identifies the identifier rank (or the relative position of the byte in the original bit-stream). FIG. 2B illustrates an example of the data at address method wherein each rank object may be combinatorially constructed from a set of components and each byte-value object may be combinatorially constructed from a set of components. Such combinatorial construction of rank and byte-value objects enables more information to be written into identifiers than if the objects where made from the single components alone (e.g., FIG. 2A).

Figure 3A:
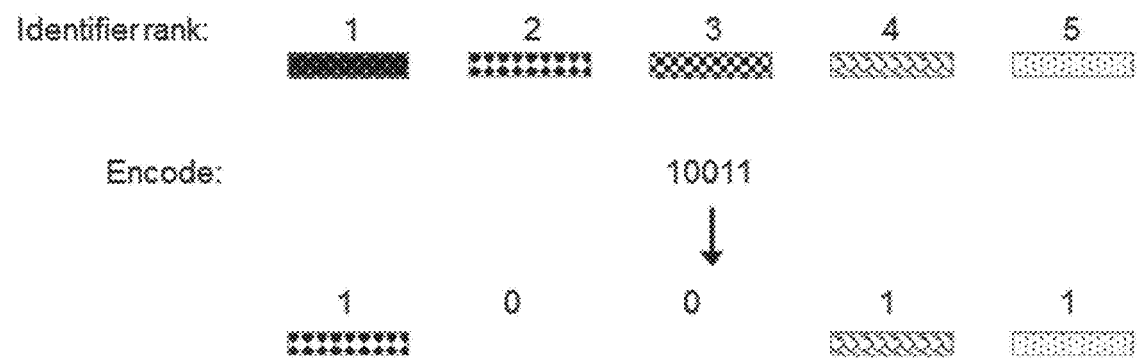
FIGS. 3A and 3B schematically illustrate an example method of encoding digital information using objects or identifiers (e.g., nucleic acid sequences)
Figure 3B:
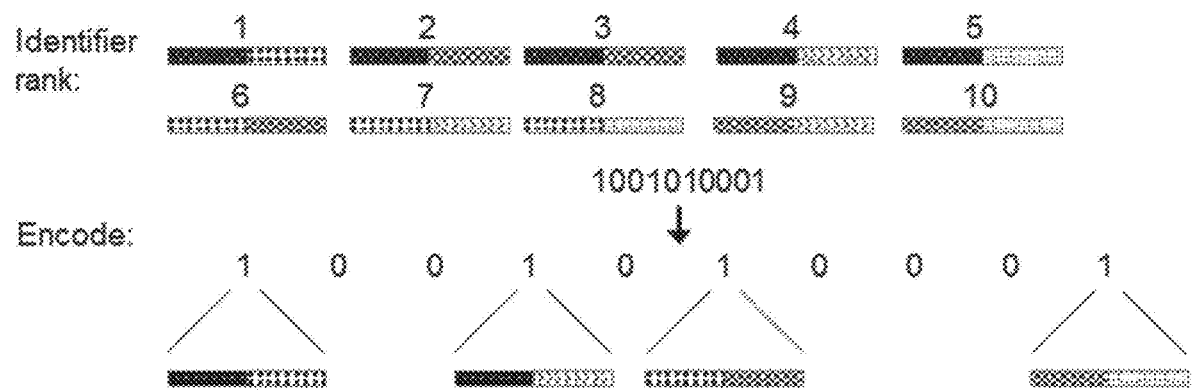

FIGS. 3A and 3B schematically illustrate another example method of encoding digital information in objects or identifiers (e.g., nucleic acid sequences). FIG. 3A illustrates encoding a bit stream into an identifier library wherein identifiers are constructed from single components that specify identifier rank. The presence of an identifier at a particular rank (or address) specifies a bit-value of '1' and the absence of an identifier at a particular rank (or address) specifies a bit-value of '0'. This type of encoding may use identifiers that solely encode rank (the relative position of a bit in the original bit stream) and use the presence or absence of those identifiers in an identifier library to encode a bit-value of '1' or '0', respectively. Reading and decoding the information may include identifying the identifiers present in the identifier library, assigning bit-values of '1' to their corresponding ranks and assigning bit-values of '0' elsewhere. FIG. 3B illustrates an example encoding method where each identifier may be combinatorially constructed from a set of components such that each possible combinatorial construction specifies a rank. Such combinatorial construction enables more information to be written into identifiers than if the identifiers where made from the single components alone (e.g., FIG. 3A). For example, a component set may comprise five distinct components. The five distinct components may be assembled to generate ten distinct identifiers, each comprising two of the five components. The ten distinct identifiers may each have a rank (or address) that corresponds to the position of a bit in a bit stream. An identifier library may include the subset of those ten possible identifiers that corresponds to the positions of bit-value '1', and exclude the subset of those ten possible identifiers that corresponds to the positions of the bit-value '0' within a bit stream of length ten.

Figure 4:
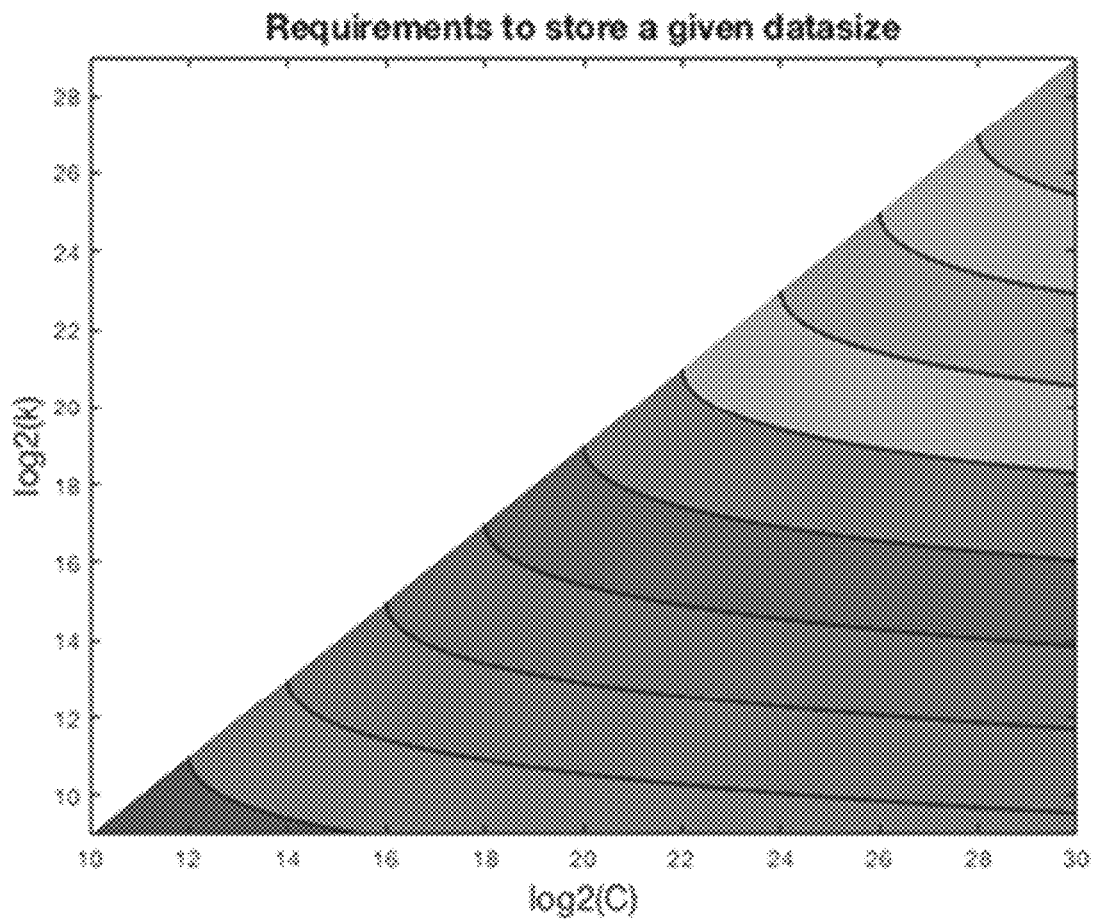
FIG. 4 shows a contour plot, in log space, of a relationship between the combinatorial space of possible identifiers (C, x-axis) and the average number of identifiers (k, y-axis) that may be constructed to store information of a given size (contour lines), according to an illustrative implementation.

FIG. 4 shows a contour plot, in log space, of a relationship between the combinatorial space of possible identifiers (C, x-axis) and the average number of identifiers (k, y-axis) to be physically constructed in order to store information of a given original size in bits (D, contour lines) using the encoding method shown in FIGS. 3A and 3B. This plot assumes that the original information of size D is re-coded into a string of C bits (where C may be greater than D) where a number of bits, k, has a bit-value of '1'. Moreover, the plot assumes that information-to-nucleic-acid encoding is performed on the re-coded bit string and that identifiers for positions where the bit-value is '1' are constructed and identifiers for positions where the bit-value is '0' are not constructed. Following the assumptions, the combinatorial space of possible identifiers has size C to identify every position in the re-coded bit string, and the number of identifiers used to encode the bit string of size D is such that $D=\log_2(Cchoosek)$, where Cchoosek may be the mathematical formula for the number of ways to pick k unordered outcomes from C possibilities. Thus, as the combinatorial space of possible identifiers increases beyond the size (in bits) of a given item of information, a decreasing number of physically constructed identifiers may be used to store the given information.

Figure 5:
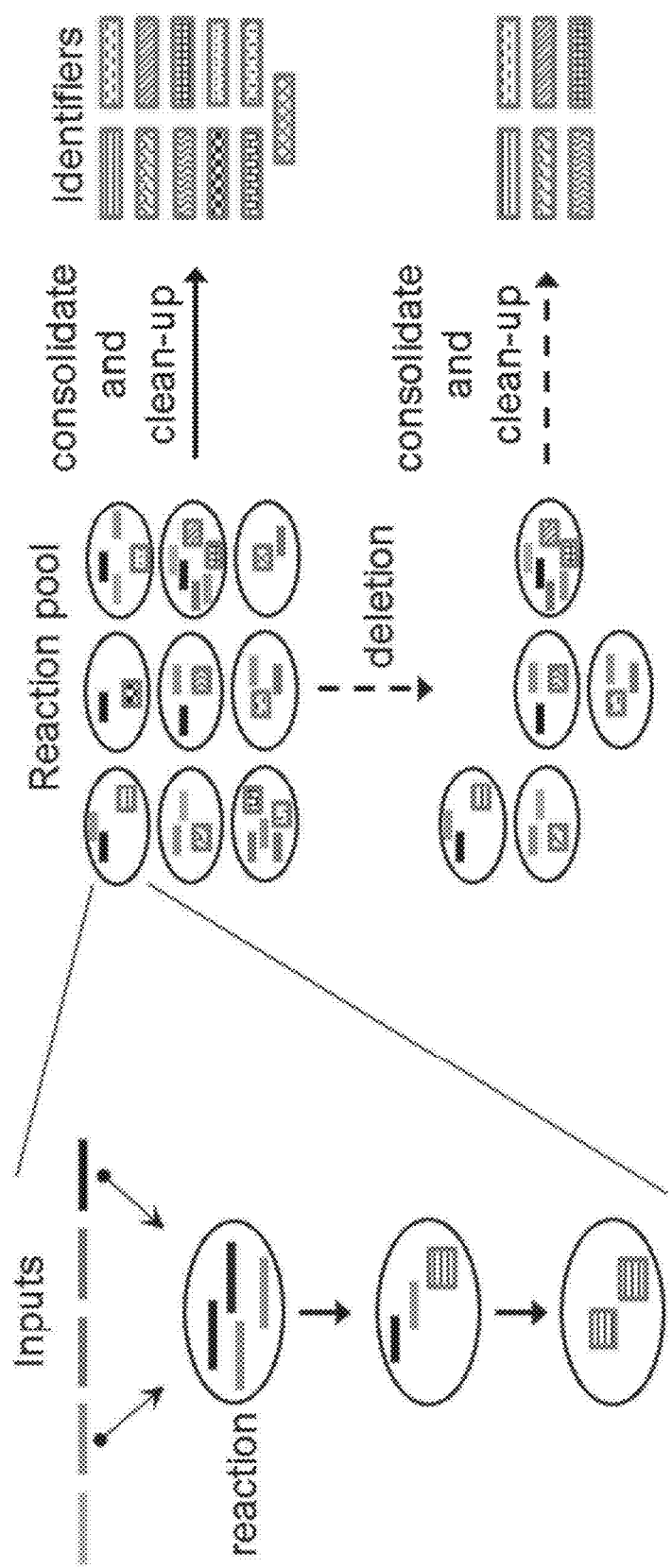
FIG. 5 schematically illustrates an overview of a method for writing information to nucleic acid sequences (e.g., deoxyribonucleic acid), according to an illustrative implementation.

FIG. 5 shows an overview method for writing information into nucleic acid sequences. Prior to writing the information, the information may be translated into a string of symbols and encoded into a plurality of identifiers. Writing the information may include setting up reactions to produce possible identifiers. A reaction may be set up by depositing inputs into a compartment. The inputs may comprise nucleic acids, components, templates, enzymes, or chemical reagents. The compartment may be a well, a tube, a position on a surface, a chamber in a microfluidic device, or a droplet within an emulsion. Multiple reactions may be set up in multiple compartments. Reactions may proceed to produce identifiers through programmed temperature incubation or cycling. Reactions may be selectively or ubiquitously removed (e.g., deleted). Reactions may also be selectively or ubiquitously interrupted, consolidated, and purified to collect their identifiers in one pool. Identifiers from multiple identifier libraries may be collected in the same pool. An individual identifier may include a barcode or a tag to identify to which identifier library it belongs. Alternatively, or in addition to, the barcode may include metadata for the encoded information. Supplemental nucleic acids or identifiers may also be included in an identifier pool together with an identifier library. The supplemental nucleic acids or identifiers may include metadata for the encoded information or serve to obfuscate or conceal the encoded information.

An identifier rank (e.g., nucleic acid index) can comprise a method or key for determining the ordering of identifiers. The method can comprise a look-up table with all identifiers and their corresponding rank. The method can also comprise a look up table with the rank of all components that constitute identifiers and a function for determining the ordering of any identifier comprising a combination of those components. Such a method may be referred to as lexicographical ordering and may be analogous to the manner in which words in a dictionary are alphabetically ordered. In the data at address encoding method, the identifier rank (encoded by the rank object of the identifier) may be used to determine the position of a byte (encoded by the byte-value object of the identifier) within a bit stream. In an alternative method, the identifier rank (encoded by the entire identifier itself) for a present identifier may be used to determine the position of bit-value of '1' within a bit stream.

A key may assign distinct bytes to unique subsets of identifiers (e.g., nucleic acid molecules) within a sample. For example, in a simple form, a key may assign each bit in a byte to a unique nucleic acid sequence that specifies the position of the bit, and then the presence or absence of that nucleic acid sequence within a sample may specify the bit-value of 1 or 0, respectively. Reading the encoded information from the nucleic acid sample can comprise any number of molecular biology techniques including sequencing, hybridization, or PCR. In some implementations, reading the encoded dataset may comprise reconstructing a portion of the dataset or reconstructing the entire encoded dataset from each nucleic acid sample. When the sequence may be read the nucleic acid index can be used along with the presence or absence of a unique nucleic acid sequence and the nucleic acid sample can be decoded into a bit stream (e.g., each string of bits, byte, bytes, or string of bytes).

Identifiers may be constructed by combinatorially assembling component nucleic acid sequences. For example, information may be encoded by taking a set of nucleic acid molecules (e.g., identifiers) from a defined group of molecules (e.g., combinatorial space). Each possible identifier of the defined group of molecules may be an assembly of nucleic acid sequences (e.g., components) from a prefabricated set of components that may be divided into layers. Each individual identifier may be constructed by concatenating one component from every layer in a fixed order. For example, if there are M layers and each layer may have n components, then up to $C=n^M$ unique identifiers may be constructed and up to $2^C$ different items of information, or C bits, may be encoded and stored. For example, storage of a megabit of information may use $1\times10^6$ distinct identifiers or a combinatorial space of size $C=1\times10^6$. The identifiers in this example may be assembled from a variety of components organized in different ways. Assemblies may be made from $M=2$ prefabricated layers, each containing $n=1\times10^3$ components. Alternatively, assemblies may be made from $M=3$ layers, each containing $n=1\times10^2$ components. As this example illustrates, encoding the same amount of information using a larger number of layers may allow for the total number of components to be smaller. Using a smaller number of total components may be advantageous in terms of writing cost.

Nucleic acid sequences (e.g., components) within each layer may comprise a unique (or distinct) sequence, or barcode, in the middle, a common hybridization region on one end, and another common hybridization region on another other end. The barcode may contain a sufficient number of nucleotides to uniquely identify every sequence within the layer. For example, there are typically four possible nucleotides for each base position within a barcode. Therefore, a three base barcode may uniquely identify $4^3=64$ nucleic acid sequences. The barcodes may be designed to be randomly generated. Alternatively, the barcodes may be designed to avoid sequences that may create complications to the construction chemistry of identifiers or sequencing. Additionally, barcodes may be designed so that each may have a minimum hamming distance from the other barcodes, thereby decreasing the likelihood that base-resolution mutations or read errors may interfere with the proper identification of the barcode.

The hybridization region on one end of the nucleic acid sequence (e.g., component) may be different in each layer, but the hybridization region may be the same for each member within a layer. Adjacent layers are those that have complementary hybridization regions on their components that allow them to interact with one another. For example, any component from layer X may be able to attach to any component from layer Y because they may have complementary hybridization regions. The hybridization region on the opposite end may serve the same purpose as the hybridization region on the first end. For example, any component from layer Y may attach to any component of layer X on one end and any component of layer Z on the opposite end.

Figure 6A:
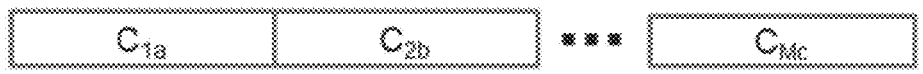
FIGS. 6A and 6B illustrate an example method, referred to as the "product scheme", for constructing identifiers (e.g., nucleic acid molecules) by combinatorially assembling distinct components (e.g., nucleic acid sequences)
Figure 6B:
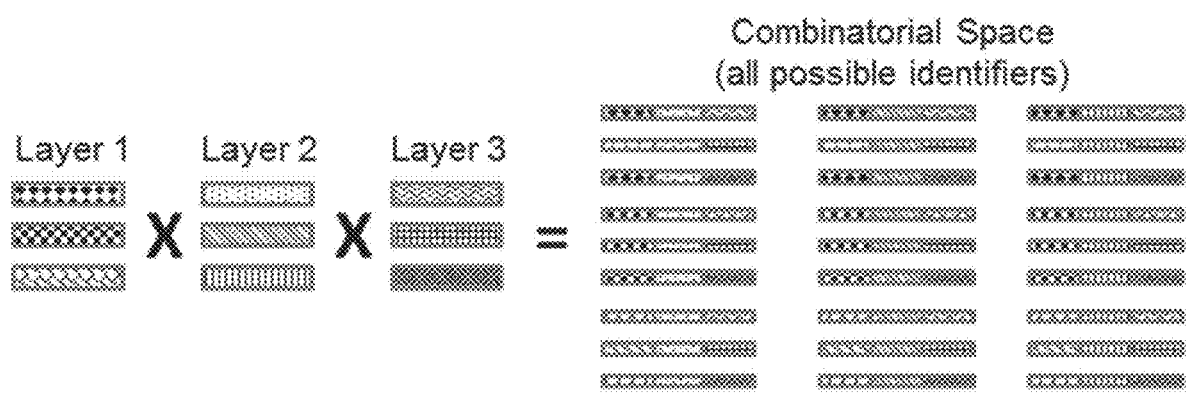

FIGS. 6A and 6B illustrate an example method, referred to as the "product scheme", for constructing identifiers (e.g., nucleic acid molecules) by combinatorially assembling a distinct component (e.g., nucleic acid sequence) from each layer in a fixed order. FIG. 6A illustrates the architecture of identifiers constructed using the product scheme. An identifier may be constructed by combining a single component from each layer in a fixed order. For M layers, each with N components, there are $N^M$ possible identifiers. FIG. 6B illustrates an example of the combinatorial space of identifiers that may be constructed using the product scheme. In an example, a combinatorial space may be generated from three layers each comprising three distinct components. The components may be combined such that one component from each layer may be combined in a fixed order. The entire combinatorial space for this assembly method may comprise twenty-seven possible identifiers.

Identifiers may be constructed using any of the implementation methods described in U.S. Pat. No. 10,650,312 entitled "NUCLEIC ACID-BASED DATA STORAGE", filed Dec. 21, 2017 (describing encoding digital information in DNA); U.S. application Ser. No. 16/461,774 entitled "SYSTEMS FOR NUCLEIC ACID-BASED DATA STORAGE", filed May 16, 2019 and published as U.S. Publication No. 2019/0362814 (describing encoding schemes for DNA-based data storage); U.S. application Ser. No. 16/414,752 entitled "PRINTER-FINISHER SYSTEM FOR DATA STORAGE IN DNA", filed May 16, 2019 and published as U.S. Publication No. 2019/0351673 (describing a printer-finisher system for assembly of encoded DNA); U.S. application Ser. No. 16/414,758 entitled "COMPOSITIONS AND METHODS FOR NUCLEIC ACID-BASED DATA STORAGE", filed May 16, 2019 and published as U.S. Publication No. 2020/0193301 (describing advanced assembly methods for DNA-based data storage); U.S. application Ser. No. 16/532,077 entitled "SYSTEMS AND METHODS FOR STORING AND READING NUCLEIC ACID-BASED DATA WITH ERROR PROTECTION", filed Aug. 5, 2019 and published as U.S. Publication No. 2020/0185057 (describing data structures and error protection and correction for DNA encoding); U.S. application Ser. No. 16/872,129 entitled "DATA STRUCTURES AND OPERATIONS FOR SEARCHING, COMPUTING, AND INDEXING IN DNA-BASED DATA STORAGE", filed May 11, 2020 (describing data structures and operations for access, rank, and search); and U.S. application Ser. No. 17/012,909 entitled "CHEMICAL METHODS FOR NUCLEIC ACID-BASED DATA STORAGE", filed Sep. 4, 2020 (describing chemical methods for encoded DNA assembly), each of which is hereby incorporated by reference in its entirety.

In some instances, all or a portion of the combinatorial space of possible identifiers may be constructed before digital information is encoded or written, and then the writing process may involve mechanically selecting and pooling the identifiers (that encode the information) from the already existing set. In other instances, the identifiers may be constructed after one or more steps of the data encoding or writing process may have occurred (i.e., as information is being written).

Barcodes can facilitate information indexing when the amount of digital information to be encoded exceeds the amount that can fit in one pool alone. Information comprising longer strings of bits and/or multiple bytes can be encoded by layering the approach disclosed in FIG. 3, for example, by including a tag with unique nucleic acid sequences encoded using the nucleic acid index. Information cassettes or identifier libraries can comprise nitrogenous bases or nucleic acid sequences that include unique nucleic acid sequences that provide location and bit-value information in addition to a barcode or tag which indicates the component or components of the bit stream that a given sequence corresponds to. Information cassettes can comprise one or more unique nucleic acid sequences as well as a barcode or tag. The barcode or tag on the information cassette can provide a reference for the information cassette and any sequences included in the information cassette. For example, the tag or barcode on an information cassette can indicate which portion of the bit stream or bit component of the bit steam the unique sequence encodes information for (e.g., the bit value and bit position information for).

Using barcodes, more information in bits can be encoded in a pool than the size of the combinatorial space of possible identifiers. A sequence of 10 bits, for example, can be separated into two sets of bytes, each byte comprising 5 bits. Each byte can be mapped to a set of 5 possible distinct identifiers. Initially, the identifiers generated for each byte can be the same, but they may be kept in separate pools or else someone reading the information may not be able to tell which byte a particular nucleic acid sequence belongs to. However each identifier can be barcoded or tagged with a label that corresponds to the byte for which the encoded information applies (e.g., barcode one may be attached to sequences in the nucleic acid pool to provide the first five bits and barcode two may be attached to sequences in the nucleic acid pool to provide the second five bits), and then the identifiers corresponding to the two bytes can be combined into one pool (e.g., "hyper-pool" or one or more identifier libraries). Each identifier library of the one or more combined identifier libraries may comprise a distinct barcode that identifies a given identifier as belonging to a given identifier library.

A nucleic acid sample pool, hyper-pool, identifier library, group of identifier libraries, or a well, containing a nucleic acid sample pool or hyper-pool may comprise unique nucleic acid molecules (e.g., identifiers) corresponding to bits of information and a plurality of supplemental nucleic acid sequences. The supplemental nucleic acid sequences may not correspond to encoded data (e.g., do not correspond to a bit value). The supplemental nucleic acid samples may mask or encrypt the information stored in the sample pool. The supplemental nucleic acid sequences may be derived from a biological source or synthetically produced. Supplemental nucleic acid sequences derived from a biological source may include randomly fragmented nucleic acid sequences or rationally fragmented sequences. The biologically derived supplemental nucleic acids may hide or obscure the data-containing nucleic acids within the sample pool by providing natural genetic information along with the synthetically encoded information, especially if the synthetically encoded information (e.g., the combinatorial space of identifiers) is made to resemble natural genetic information (e.g., a fragmented genome). In an example, the identifiers are derived from a biological source and the supplemental nucleic acids are derived from a biological source. A sample pool may contain multiple sets of identifiers and supplemental nucleic acid sequences. Each set of identifiers and supplemental nucleic acid sequences may be derived from different organisms. In an example, the identifiers are derived from one or more organisms and the supplemental nucleic acid sequences are derived from a single, different organism. The supplemental nucleic acid sequences may also be derived from one or more organism and the identifiers may be derived from a single organism that is different from the organism that the supplemental nucleic acids are derived from. Both the identifiers and the supplemental nucleic acid sequences may be derived from multiple different organisms. A key may be used to distinguish the identifiers from the supplemental nucleic acid sequences.

The supplemental nucleic acid sequences may store metadata about the written information. The metadata may comprise extra information for determining and/or authorizing the source of the original information and or the intended recipient of the original information. The metadata may comprise extra information about the format of the original information, the instruments and methods used to encode and write the original information, and the date and time of writing the original information into the identifiers. The metadata may comprise additional information about the format of the original information, the instruments and methods used to encode and write the original information, and the date and time of writing the original information into nucleic acid sequences. The metadata may comprise additional information about modifications made to the original information after writing the information into nucleic acid sequences. The metadata may comprise annotations to the original information or one or more references to external information. Alternatively, or in addition to, the metadata may be stored in one or more barcodes or tags attached to the identifiers.

The identifiers in an identifier pool may have the same, similar, or different lengths than one another. The supplemental nucleic acid sequences may have a length that is less than, substantially equal to, or greater than the length of the identifiers. The supplemental nucleic acid sequences may have an average length that is within one base, within two bases, within three bases, within four bases, within five bases, within six bases, within seven bases, within eight bases, within nine bases, within ten bases, or within more bases of the average length of the identifiers. In an example, the supplemental nucleic acid sequences are the same or substantially the same length as the identifiers. The concentration of supplemental nucleic acid sequences may be less than, substantially equal to, or greater than the concentration of the identifiers in the identifiers library. The concentration of the supplemental nucleic acids may be less than or equal to about 1%, 10%, 20%, 40%, 60%, 80%, 100, %, 125%, 150%, 175%, 200%, 1000%, $1 \times 10^4$%, $1 \times 10^5$%, $1 \times 10^6$%, $1 \times 10^7$%, $1 \times 10^8$% or less than the concentration of the identifiers. The concentration of the supplemental nucleic acids may be greater than or equal to about 1%, 10%, 20%, 40%, 60%, 80%, 100, %, 125%, 150%, 175%, 200%, 1000%, $1 \times 10^4$%, $1 \times 10^5$%, $1 \times 10^6$%, $1 \times 10^7$%, $1 \times 10^8$% or more than the concentration of the identifiers. Larger concentrations may be beneficial for obfuscation or concealing data. In an example, the concentration of the supplemental nucleic acid sequences are substantially greater (e.g., $1 \times 10^8$% greater) than the concentration of identifiers in an identifier pool.

PCR based methods can be used to access and copy data from identifier or nucleic acid sample pools. Using common primer binding sites that flank the identifiers in the pools or hyper-pools, nucleic acids containing information can be readily copied. Alternatively, other nucleic acid amplification approaches such as isothermal amplification may also be used to readily copy data from sample pools or hyper-pools (e.g., identifier libraries). See Chemical Methods Section D on nucleic acid amplification. In instances where the sample comprises hyper-pools, a particular subset of information (e.g., all nucleic acids relating to a particular barcode) can be accessed and retrieved by using a primer that binds the specific barcode at one edge of the identifier in the forward orientation, along with another primer that binds a common sequence on the opposite edge of the identifier in a reverse orientation. Various read-out methods can be used to pull information from the encoded nucleic acid; for example microarray (or any sort of fluorescent hybridization), digital PCR, quantitative PCR (qPCR), and various sequencing platforms can be further used to read out the encoded sequences and by extension digitally encoded data.

Figure 7A:
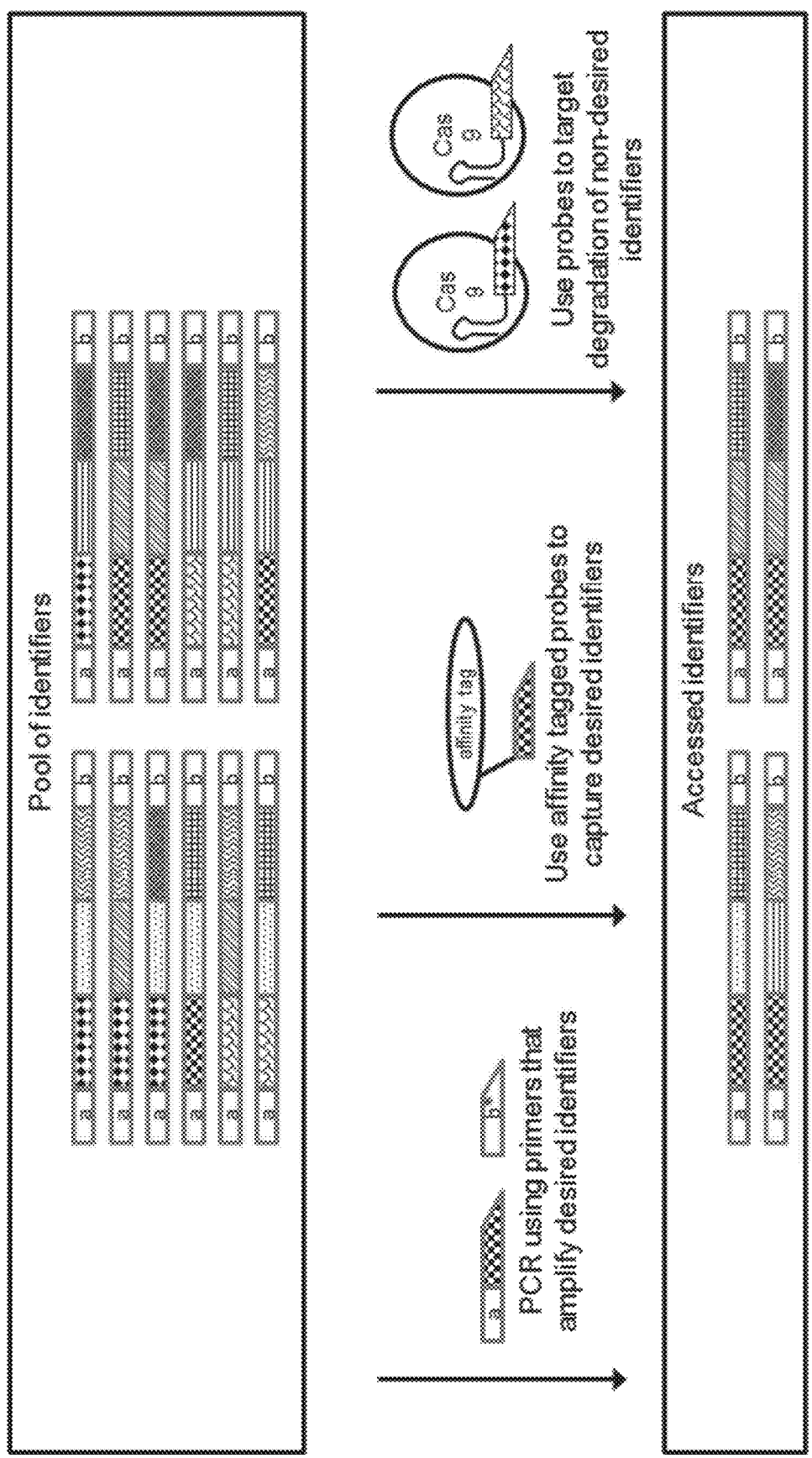
FIGS. 7A-7C schematically illustrate an overview of example methods for accessing portions of information stored in nucleic acid sequences by accessing a number of particular identifiers from a larger number of identifiers.
Figure 7B:
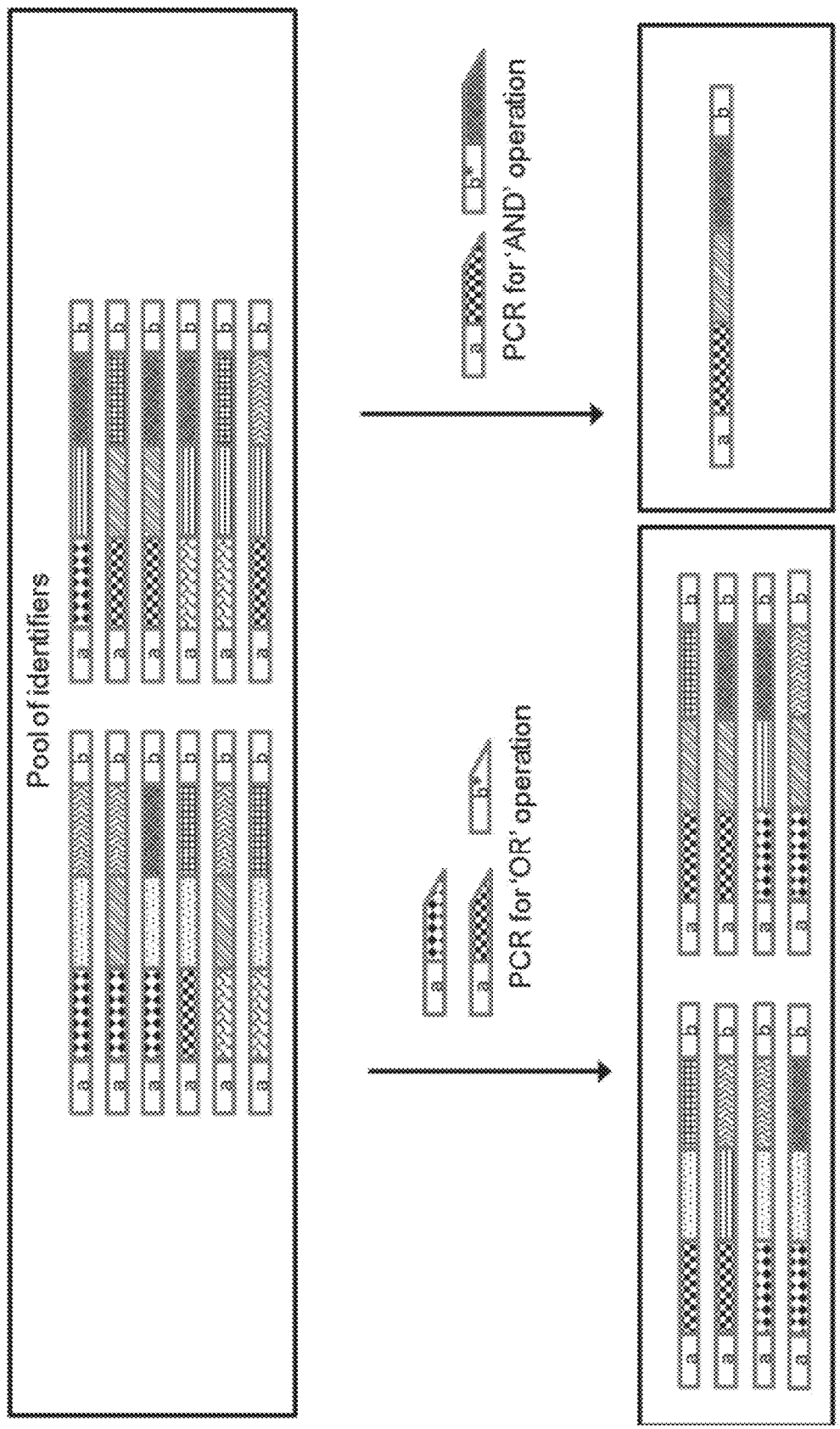
Figure 7C:
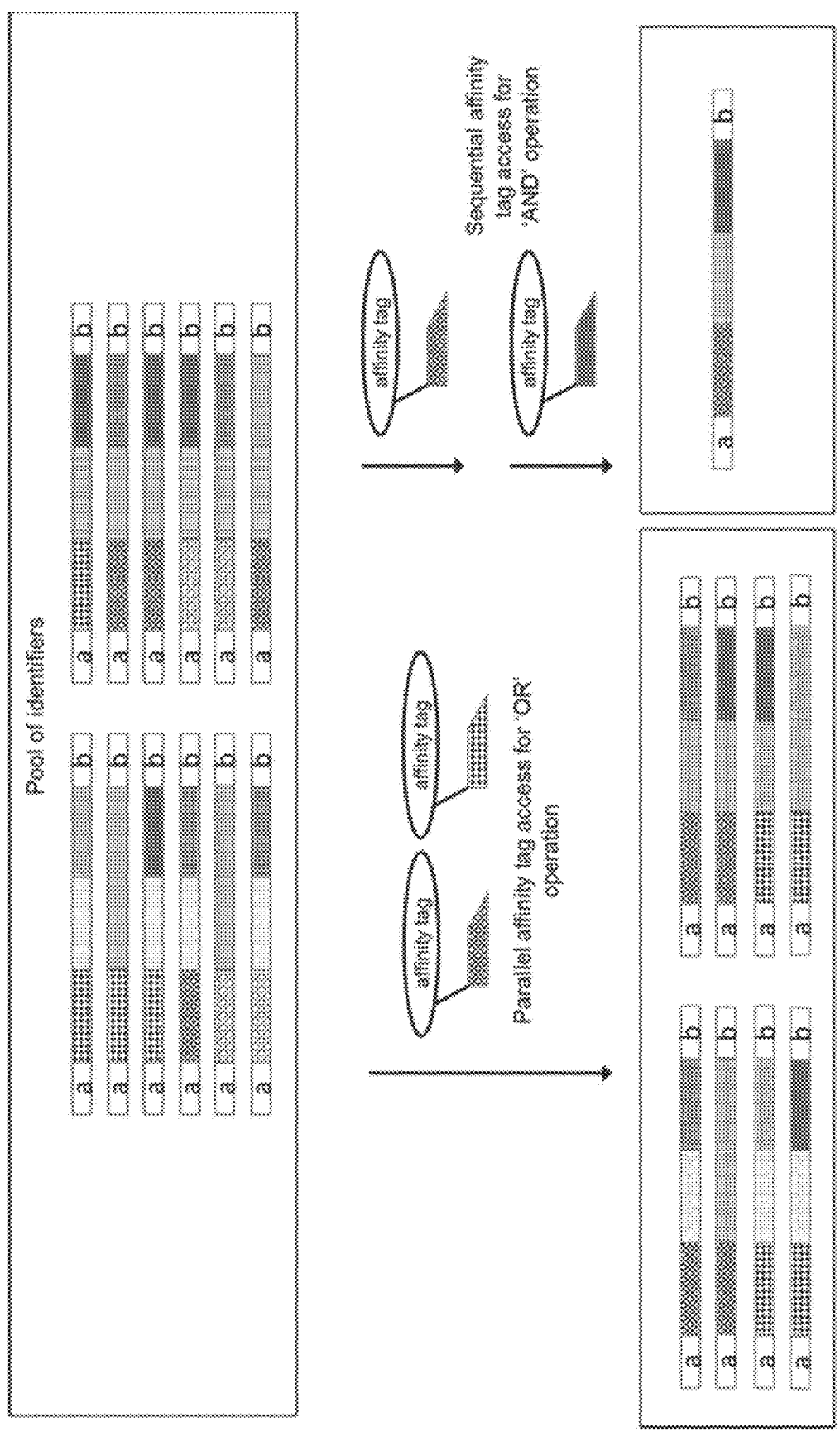

Accessing information stored in nucleic acid molecules (e.g., identifiers) may be performed by selectively removing the portion of non-targeted identifiers from an identifier library or a pool of identifiers or, for example, selectively removing all identifiers of an identifier library from a pool of multiple identifier libraries. As used herein, "access" and "query" can be used interchangeably. Accessing data may also be performed by selectively capturing targeted identifiers from an identifier library or pool of identifiers. The targeted identifiers may correspond to data of interest within the larger item of information. A pool of identifiers may comprise supplemental nucleic acid molecules. The supplemental nucleic acid molecules may contain metadata about the encoded information or may be used to encrypt or mask the identifiers corresponding to the information. The supplemental nucleic acid molecules may or may not be extracted while accessing the targeted identifiers. FIGS. 7A-7C schematically illustrate an overview of example methods for accessing portions of information stored in nucleic acid sequences by accessing a number of particular identifiers from a larger number of identifiers. FIG. 7A shows example methods for using polymerase chain reaction, affinity tagged probes, and degradation targeting probes to access identifiers containing a specified component. For PCR-based access, a pool of identifiers (e.g., identifier library) may comprise identifiers with a common sequence at each end, a variable sequence at each end, or one of a common sequence or a variable sequence at each end. The common sequences or variable sequences may be primer binding sites. One or more primers may bind to the common or variable regions on the identifier edges. The identifiers with primers bound may be amplified by PCR. The amplified identifiers may significantly outnumber the non-amplified identifiers. During reading, the amplified identifiers may be identified. An identifier from an identifier library may comprise sequences on one or both of its ends that are distinct to that library, thus enabling a single library to be selectively accessed from a pool or group of more than one identifier libraries.

For affinity-tag based access, a process which may be referred to as nucleic acid capture, the components that constitute the identifiers in a pool may share complementarity with one or more probes. The one or more probes may bind or hybridize to the identifiers to be accessed. The probe may comprise an affinity tag. The affinity tags may bind to a bead, generating a complex comprising a bead, at least one probe, and at least one identifier. The beads may be magnetic, and together with a magnet, the beads may collect and isolate the identifiers to be accessed. The identifiers may be removed from the beads under denaturing conditions prior to reading. Alternatively, or in addition to, the beads may collect the non-targeted identifiers and sequester them away from the rest of the pool that can get washed into a separate vessel and read. The affinity tag may bind to a column. The identifiers to be accessed may bind to the column for capture. Column-bound identifiers may subsequently be eluted or denatured from the column prior to reading. Alternatively, the non-targeted identifiers may be selectively targeted to the column while the targeted identifiers may flow through the column. Accessing the targeted identifiers may comprise applying one or more probes to a pool of identifiers simultaneously or applying one or more probes to a pool of identifiers sequentially.

For degradation based access, the components that constitute the identifiers in a pool may share complementarity with one or more degradation-targeting probes. The probes may bind to or hybridize with distinct components on the identifiers. The probe may be a target for a degradation enzyme, such as an endonuclease. In an example, one or more identifier libraries may be combined. A set of probes may hybridize with one of the identifier libraries. The set of probes may comprise RNA and the RNA may guide a Cas9 enzyme. A Cas9 enzyme may be introduced to the one or more identifier libraries. The identifiers hybridized with the probes may be degraded by the Cas9 enzyme. The identifiers to be accessed may not be degraded by the degradation enzyme. In another example, the identifiers may be single-stranded and the identifier library may be combined with a single-strand specific endonuclease(s), such as the S1 nuclease, that selectively degrades identifiers that are not to be accessed. Identifiers to be accessed may be hybridized with a complementary set of identifiers to protect them from degradation by the single-strand specific endonuclease(s). The identifiers to be accessed may be separated from the degradation products by size selection, such as size selection chromatography (e.g., agarose gel electrophoresis). Alternatively, or in addition, identifiers that are not degraded may be selectively amplified (e.g., using PCR) such that the degradation products are not amplified. The non-degraded identifiers may be amplified using primers that hybridize to each end of the non-degraded identifiers and therefore not to each end of the degraded or cleaved identifiers.

FIG. 7B shows example methods for using polymerase chain reaction to perform 'OR' or 'AND' operations to access identifiers containing multiple components. In an example, if two forward primers bind distinct sets of identifiers on the left end, then an 'OR' amplification of the union of those sets of identifiers may be accomplished by using the two forward primers together in a multiplex PCR reaction with a reverse primer that binds all of the identifiers on the right end. In another example, if one forward primer binds a set of identifiers on the left end and one reverse primer binds a set of identifiers on the right end, then an 'AND' amplification of the intersection of those two sets of identifiers may be accomplished by using the forward primer and the reverse primer together as a primer pair in a PCR reaction.

FIG. 7C shows example methods for using affinity tags to perform 'OR' or 'AND' operations to access identifiers containing multiple components. In an example, if affinity probe 'P1' captures all identifiers with component 'C1' and another affinity probe 'P2' captures all identifiers with component 'C2', then the set of all identifiers with C1 or C2 can be captured by using P1 and P2 simultaneously (corresponding to an 'OR' operation). In another example with the same components and probes, the set of all identifiers with C1 and C2 can be captures by using P1 and P2 sequentially (corresponding to an 'AND' operation).

In another aspect, the present disclosure provides methods for reading information encoded in nucleic acid sequences. A method for reading information encoded in nucleic acid sequences may comprise (a) providing an identifier library, (b) identifying the identifiers present in the identifier library, (c) generating a string of symbols from the identifiers present in the identifier library, and (d) compiling information from the string of symbols. An identifier library may comprise a subset of a plurality of identifiers from a combinatorial space. Each individual identifier of the subset of identifiers may correspond to an individual symbol in a string of symbols. An identifier may comprise one or more components. A component may comprise a nucleic acid sequence.

Information may be written into one or more identifier libraries as described elsewhere herein. Identifiers may be constructed using any method described elsewhere herein. Stored data may be copied and accessed using any method described elsewhere herein.

The identifier may comprise information relating to a location of the encoded symbol, a value of the encoded symbol, or both the location and the value of the encoded symbol. An identifier may include information relating to a location of the encoded symbol and the presence or absence of the identifier in an identifier library may indicate the value of the symbol. The presence of an identifier in an identifier library may indicate a first symbol value (e.g., first bit value) in a binary string and the absence of an identifier in an identifier library may indicate a second symbol value (e.g., second bit value) in a binary string. In a binary system, basing a bit value on the presence or absence of an identifier in an identifier library may reduce the number of identifiers assembled and, therefore, reduce the write time. In an example, the presence of an identifier may indicate a bit value of '1' at the mapped location and the absence of an identifier may indicate a bit value of '0' at the mapped location.

Generating symbols (e.g., bit values) for a piece of information may include identifying the presence or absence of the identifier that the symbol (e.g., bit) may be mapped or encoded to. Determining the presence or absence of an identifier may include sequencing the present identifiers or using a hybridization array to detect the presence of an identifier. In an example, decoding and reading the encoded sequences may be performed using sequencing platforms. Examples of sequencing platforms are described in U.S. application Ser. No. 16/532,077 entitled "SYSTEMS AND METHODS FOR STORING AND READING NUCLEIC ACID-BASED DATA WITH ERROR PROTECTION", filed Aug. 5, 2019 and published as U.S. Publication No. 2020/0185057, which is entirely incorporated herein by reference.

In an example, decoding nucleic acid encoded data may be achieved by base-by-base sequencing of the nucleic acid strands, such as Illumina® Sequencing, or by utilizing a sequencing technique that indicates the presence or absence of specific nucleic acid sequences, such as fragmentation analysis by capillary electrophoresis. The sequencing may employ the use of reversible terminators. The sequencing may employ the use of natural or non-natural (e.g., engineered) nucleotides or nucleotide analogs. Alternatively or in addition to, decoding nucleic acid sequences may be performed using a variety of analytical techniques, including but not limited to, any methods that generate optical, electrochemical, or chemical signals. A variety of sequencing approaches may be used including, but not limited to, polymerase chain reaction (PCR), digital PCR, Sanger sequencing, high-throughput sequencing, sequencing-by-synthesis, single-molecule sequencing, sequencing-by-ligation, RNA-Seq (Illumina), Next generation sequencing, Digital Gene Expression (Helicos), Clonal Single MicroArray (Solexa), shotgun sequencing, Maxim-Gilbert sequencing, or massively-parallel sequencing.

Various read-out methods can be used to pull information from the encoded nucleic acid. In an example, microarray (or any sort of fluorescent hybridization), digital PCR, quantitative PCR (qPCR), and various sequencing platforms can be further used to read out the encoded sequences and by extension digitally encoded data.

An identifier library may further comprise supplemental nucleic acid sequences that provide metadata about the information, encrypt or mask the information, or that both provide metadata and mask the information. The supplemental nucleic acids may be identified simultaneously with identification of the identifiers. Alternatively, the supplemental nucleic acids may be identified prior to or after identifying the identifiers. In an example, the supplemental nucleic acids are not identified during reading of the encoded information. The supplemental nucleic acid sequences may be indistinguishable from the identifiers. An identifier index or a key may be used to differentiate the supplemental nucleic acid molecules from the identifiers.

The efficiency of encoding and decoding data may be increased by recoding input bit strings to enable the use of fewer nucleic acid molecules. For example, if an input string is received with a high occurrence of '111' substrings, which may map to three nucleic acid molecules (e.g., identifiers) with an encoding method, it may be recoded to a '000' substring which may map to a null set of nucleic acid molecules. The alternate input substring of '000' may also be recoded to '111'. This method of recoding may reduce the total amount of nucleic acid molecules used to encode the data because there may be a reduction in the number of '1's in the dataset. In this example, the total size of the dataset may be increased to accommodate a codebook that specifies the new mapping instructions. An alternative method for increasing encoding and decoding efficiency may be to recode the input string to reduce the variable length. For example, '111' may be recoded to '00' which may shrink the size of the dataset and reduce the number of '1's in the dataset.

The speed and efficiency of decoding nucleic acid encoded data may be controlled (e.g., increased) by specifically designing identifiers for ease of detection. For example, nucleic acid sequences (e.g., identifiers) that are designed for ease of detection may include nucleic acid sequences comprising a majority of nucleotides that are easier to call and detect based on their optical, electrochemical, chemical, or physical properties. Engineered nucleic acid sequences may be either single or double stranded. Engineered nucleic acid sequences may include synthetic or unnatural nucleotides that improve the detectable properties of the nucleic acid sequence. Engineered nucleic acid sequences may comprise all natural nucleotides, all synthetic or unnatural nucleotides, or a combination of natural, synthetic, and unnatural nucleotides. Synthetic nucleotides may include nucleotide analogues such as peptide nucleic acids, locked nucleic acids, glycol nucleic acids, and threose nucleic acids. Unnatural nucleotides may include dNaM, an artificial nucleoside containing a 3-methoxy-2-naphthly group, and d5SICS, an artificial nucleoside containing a 6-methylisoquinoline-1-thione-2-yl group. Engineered nucleic acid sequences may be designed for a single enhanced property, such as enhanced optical properties, or the designed nucleic acid sequences may be designed with multiple enhanced properties, such as enhanced optical and electrochemical properties or enhanced optical and chemical properties.

Engineered nucleic acid sequences may comprise reactive natural, synthetic, and unnatural nucleotides that do not improve the optical, electrochemical, chemical, or physical properties of the nucleic acid sequences. The reactive components of the nucleic acid sequences may enable the addition of a chemical moiety that confers improved properties to the nucleic acid sequence. Each nucleic acid sequence may include a single chemical moiety or may include multiple chemical moieties. Example chemical moieties may include, but are not limited to, fluorescent moieties, chemiluminescent moieties, acidic or basic moieties, hydrophobic or hydrophilic moieties, and moieties that alter oxidation state or reactivity of the nucleic acid sequence.

A sequencing platform may be designed specifically for decoding and reading information encoded into nucleic acid sequences. The sequencing platform may be dedicated to sequencing single or double stranded nucleic acid molecules. The sequencing platform may decode nucleic acid encoded data by reading individual bases (e.g., base-by-base sequencing) or by detecting the presence or absence of an entire nucleic acid sequence (e.g., component) incorporated within the nucleic acid molecule (e.g., identifier). The sequencing platform may include the use of promiscuous reagents, increased read lengths, and the detection of specific nucleic acid sequences by the addition of detectable chemical moieties. The use of more promiscuous reagents during sequencing may increase reading efficiency by enabling faster base calling which in turn may decrease the sequencing time. The use of increased read lengths may enable longer sequences of encoded nucleic acids to be decoded per read. The addition of detectable chemical moiety tags may enable the detection of the presence or absence of a nucleic acid sequence by the presence or absence of a chemical moiety. For example, each nucleic acid sequence encoding a bit of information may be tagged with a chemical moiety that generates a unique optical, electrochemical, or chemical signal. The presence or absence of that unique optical, electrochemical, or chemical signal may indicate a '0' or a '1' bit value. The nucleic acid sequence may comprise a single chemical moiety or multiple chemical moieties. The chemical moiety may be added to the nucleic acid sequence prior to use of the nucleic acid sequence to encode data. Alternatively or in addition to, the chemical moiety may be added to the nucleic acid sequence after encoding the data, but prior to decoding the data. The chemical moiety tag may be added directly to the nucleic acid sequence or the nucleic acid sequence may comprise a synthetic or unnatural nucleotide anchor and the chemical moiety tag may be added to that anchor.

Unique codes may be applied to minimize or detect encoding and decoding errors. Encoding and decoding errors may occur from false negatives (e.g., a nucleic acid molecule or identifier not included in a random sampling). An example of an error detecting code may be a checksum sequence that counts the number of identifiers in a contiguous set of possible identifiers that is included in the identifier library. While reading the identifier library, the checksum may indicate how many identifiers from that contiguous set of identifiers to expect to retrieve, and identifiers can continue to be sampled for reading until the expected number is met. In some implementations, a checksum sequence may be included for every contiguous set of R identifiers where R can be equal in size or greater than 1, 2, 5, 10, 50, 100, 200, 500, or 1000 or less than 1000, 500, 200, 100, 50, 10, 5, or 2. The smaller the value of R, the better the error detection. In some implementations, the checksums may be supplemental nucleic acid sequences. For example, a set comprising seven nucleic acid sequences (e.g., components) may be divided into two groups, nucleic acid sequences for constructing identifiers with a product scheme (components X1-X3 in layer X and Y1-Y3 in layer Y), and nucleic acid sequences for the supplemental checksums (X4-X7 and Y4-Y7). The checksum sequences X4-X7 may indicate whether zero, one, two, or three sequences of layer X are assembled with each member of layer Y. Alternatively, the checksum sequences Y4-Y7 may indicate whether zero, one, two, or three sequences of layer Y are assembled with each member of layer X. In this example, an original identifier library with identifiers {X1Y1, X1Y3, X2Y1, X2Y2, X2Y3} may be supplemented to include checksums to become the following pool: {X1Y1, X1Y3, X2Y1, X2Y2, X2Y3, X1Y6, X2Y7, X3Y4, X6Y1, X5Y2, X6Y3}. The checksum sequences may also be used for error correction. For example, absence of X1Y1 from the above dataset and the presence of X1Y6 and X6Y1 may enable inference that the X1Y1 nucleic acid molecule is missing from the dataset. The checksum sequences may indicate whether identifiers are missing from a sampling of the identifier library or an accessed portion of the identifier library. In the case of a missing checksum sequence, access methods such as PCR or affinity tagged probe hybridization may amplify and/or isolate it. In some implementations, the checksums may not be supplemental nucleic acid sequences. They checksums may be coded directly into the information such that they are represented by identifiers.

Noise in data encoding and decoding may be reduced by constructing identifiers palindromically, for example, by using palindromic pairs of components rather than single components in the product scheme. Then the pairs of components from different layers may be assembled to one another in a palindromic manner (e.g., YXY instead of XY for components X and Y). This palindromic method may be expanded to larger numbers of layers (e.g., ZYXYZ instead of XYZ) and may enable detection of erroneous cross reactions between identifiers.

Adding supplemental nucleic acid sequences in excess (e.g., vast excess) to the identifiers may prevent sequencing from recovering the encoded identifiers. Prior to decoding the information, the identifiers may be enriched from the supplemental nucleic acid sequences. For example, the identifiers may be enriched by a nucleic acid amplification reaction using primers specific to the identifier ends. Thus only an entity in possession of the identifier-specific primers or the sequences of the identifier-specific primers would be able to enrich the encoded identifiers for recovery via sequencing. Alternatively, or in addition to, the information may be decoded without enriching the sample pool by sequencing (e.g., sequencing by synthesis) using a specific primer. In both decoding methods, it may be difficult to enrich or decode the information without having a decoding key or knowing something about the composition of the identifiers. Alternative access methods may also be employed such as using affinity tag based probes.

A system for encoding digital information into nucleic acids (e.g., DNA) can comprise systems, methods and devices for converting files and data (e.g., raw data, compressed zip files, integer data, and other forms of data) into bytes and encoding the bytes into segments or sequences of nucleic acids, typically DNA, or combinations thereof.

Non-limiting implementations of methods for using the system to encode digital data can comprise steps for receiving digital information in the form of byte streams. Parsing the byte streams into individual bytes, mapping the location of a bit within the byte using a nucleic acid index (or identifier rank), and encoding sequences corresponding to either bit values of 1 or bit values of 0 into identifiers. Steps for retrieving digital data can comprise sequencing a nucleic acid sample or nucleic acid pool comprising sequences of nucleic acid (e.g., identifiers) that map to one or more bits, referencing an identifier rank to confirm if the identifier is present in the nucleic acid pool and decoding the location and bit-value information for each sequence into a byte comprising a sequence of digital information.

Systems for encoding, writing, copying, accessing, reading, and decoding information encoded and written into nucleic acid molecules may be a single integrated unit or may be multiple units configured to execute one or more of the aforementioned operations. A system for encoding and writing information into nucleic acid molecules (e.g., identifiers) may include a device and one or more computer processors. The one or more computer processors may be programmed to parse the information into strings of symbols (e.g., strings of bits). The computer processor may generate an identifier rank. The computer processor may categorize the symbols into two or more categories. One category may include symbols to be represented by a presence of the corresponding identifier in the identifier library and the other category may include symbols to be represented by an absence of the corresponding identifiers in the identifier library. The computer processor may direct the device to assemble the identifiers corresponding to symbols to be represented to the presence of an identifier in the identifier library. An suitable system is described in U.S. application Ser. No. 16/414,752 entitled "PRINTER-FINISHER SYSTEM FOR DATA STORAGE IN DNA", filed May 16, 2019 and published as U.S. Publication No. 2019/0351673.

The device may comprise a plurality regions, sections, or partitions. The reagents and components to assemble the identifiers may be stored in one or more regions, sections, or partitions of the device. Layers may be stored in separate regions of section of the device. A layer may comprise one or more unique components. The component in one layer may be unique from the components in another layer. The regions or sections may comprise vessels and the partitions may comprise wells. Each layer may be stored in a separate vessel or partition. Each reagent or nucleic acid sequence may be stored in a separate vessel or partition. Alternatively, or in addition to, reagents may be combined to form a master mix for identifier construction. The device may transfer reagents, components, and templates from one section of the device to be combined in another section. The device may provide the conditions for completing the assembly reaction. For example, the device may provide heating, agitation, and detection of reaction progress. The constructed identifiers may be directed to undergo one or more subsequent reactions to add barcodes, common sequences, variable sequences, or tags to one or more ends of the identifiers. The identifiers may then be directed to a region or partition to generate an identifier library. One or more identifier libraries may be stored in each region, section, or individual partition of the device. The device may transfer fluid (e.g., reagents, components, templates) using pressure, vacuum, or suction.

The identifier libraries may be stored in the device, moved to a separate database, or transferred to a suitable composition or container for tagging/tracking artifacts. The database may comprise one or more identifier libraries. The database may provide conditions for long term storage of the identifier libraries (e.g., conditions to reduce degradation of identifiers). The identifier libraries may be stored in a powder, liquid, or solid form. Aqueous solutions of identifiers may be lyophilized for more stable storage. The database may provide Ultra-Violet light protection, reduced temperature (e.g., refrigeration or freezing), and protection from degrading chemicals and enzymes. Prior to being transferred to a database or functionalized to an artifact, the identifier libraries may be lyophilized or frozen. The identifier libraries may include ethylenediaminetetraacetic acid (EDTA) to inactivate nucleases and/or a buffer to maintain the stability of the nucleic acid molecules.

The database may be coupled to, include, or be separate from a device that writes the information into identifiers, copies the information, accesses the information, or reads the information. A portion of an identifier library may be removed from the database prior to copying, accessing or reading. The device that copies the information from the database may be the same or a different device from that which writes the information. The device that copies the information may extract an aliquot of an identifier library from the device and combine that aliquot with the reagents and constituents to amplify a portion of or the entire identifier library. The device may control the temperature, pressure, and agitation of the amplification reaction. The device may comprise partitions and one or more amplification reaction may occur in the partition comprising the identifier library. The device may copy more than one pool of identifiers at a time.

The accessed data may be read in the same device or the accessed data may be transferred to another device. The reading device may comprise a detection unit to detect and identify the identifiers. The detection unit may be part of a sequencer, hybridization array, or other unit for identifying the presence or absence of an identifier. A sequencing platform may be designed specifically for decoding and reading information encoded into nucleic acid sequences. The sequencing platform may be dedicated to sequencing single or double stranded nucleic acid molecules. The sequencing platform may decode nucleic acid encoded data by reading individual bases (e.g., base-by-base sequencing) or by detecting the presence or absence of an entire nucleic acid sequence (e.g., component) incorporated within the nucleic acid molecule (e.g., identifier). Alternatively, the sequencing platform may be a system such as Illumina® Sequencing or fragmentation analysis by capillary electrophoresis. Alternatively or in addition to, decoding nucleic acid sequences may be performed using a variety of analytical techniques implemented by the device, including but not limited to, any methods that generate optical, electrochemical, or chemical signals.

Information storage in nucleic acid molecules may have various applications including, but not limited to, long term information storage, sensitive information storage, storage of one-time access codes, and storage of medical information. In an example, a person's medical information (e.g., medical history and records) may be stored in nucleic acid molecules and carried on his or her person. The information may be stored external to the body (e.g., in a wearable device) or internal to the body (e.g., in a subcutaneous capsule). When a patient is brought into a medical office or hospital, a sample may be taken from the device or capsule and the information may be decoded with the use of a nucleic acid sequencer. Personal storage of medical records in nucleic acid molecules may provide an alternative to computer and cloud based storage systems. Personal storage of medical records in nucleic acid molecules may reduce the instance or prevalence of medical records being hacked. Nucleic acid molecules used for capsule-based storage of medical records may be derived from human genomic sequences. The use of human genomic sequences may decrease the immunogenicity of the nucleic acid sequences in the event of capsule failure and leakage.

Figure 8:
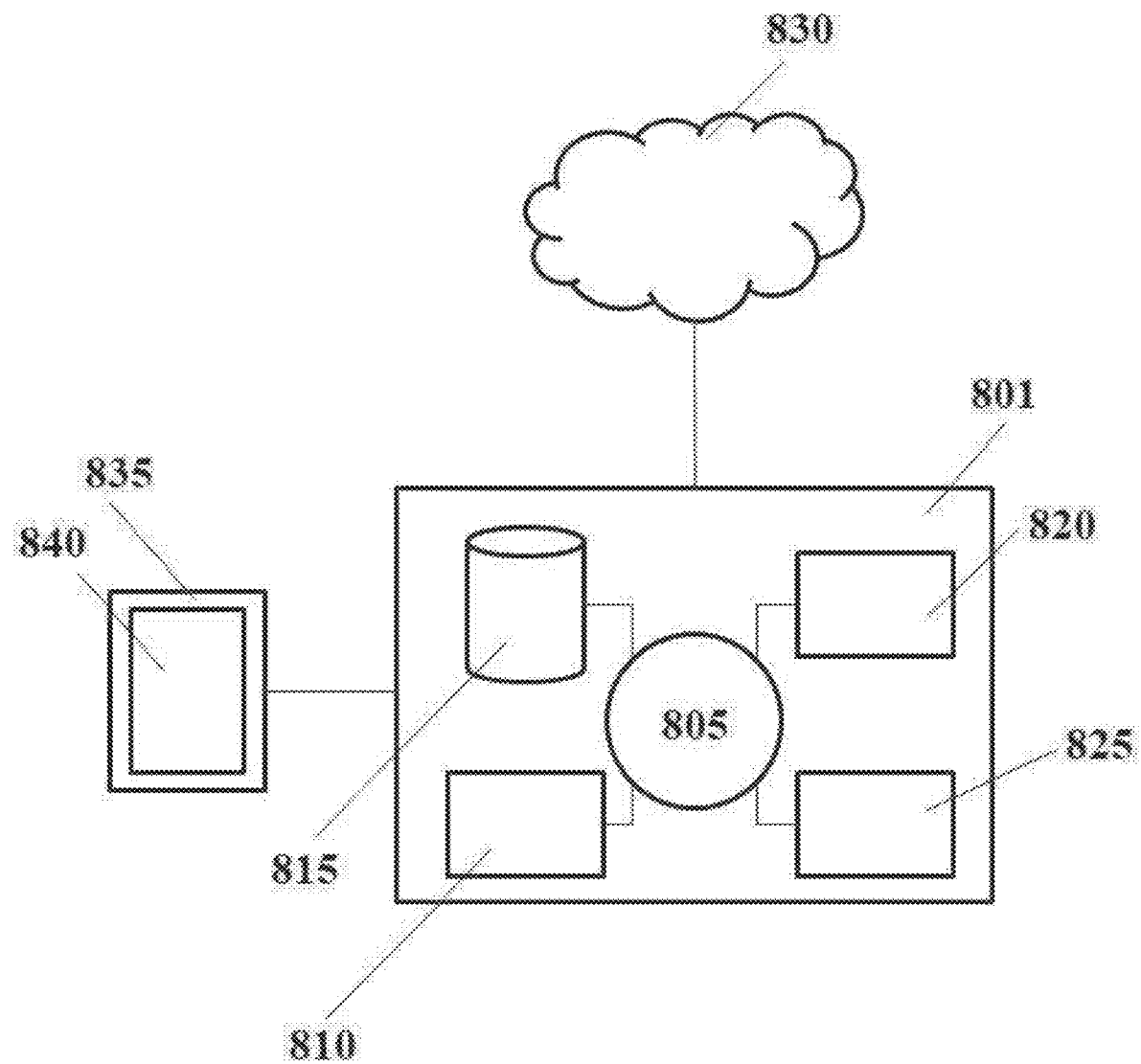
FIG. 8 shows a computer system that is programmed or otherwise configured to implement methods provided herein, according to an illustrative implementation.

The present disclosure provides computer systems that are programmed to implement methods of the disclosure. FIG. 8 shows a computer system 801 that is programmed or otherwise configured to encode digital information into nucleic acid sequences and/or read (e.g., decode) information derived from nucleic acid sequences. The computer system 801 can regulate various aspects of the encoding and decoding procedures of the present disclosure, such as, for example, the bit-values and bit location information for a given bit or byte from an encoded bitstream or byte stream.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user or other devices and or machinery that may be used by the user in the course of analyzing data encoded or decoded in a sequence of nucleic acids (e.g., a sequencer or other system for chemically determining the order of nitrogenous bases in a nucleic acid sequence). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810. Computer system 801 may be operatively coupled to any one of a sequencing machine, a barcode scanner, a retina scanner, a fingerprint scanner, a keypad entry device, a swabbing device, and an automated liquid handling unit configured to perform any of the chemical methods and operation described herein. Computer system 801 may be configured to lock and unlock physical access to a secured location or deposit.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840 for providing, for example, sequence output data including chromatographs, sequences as well as bits, bytes, or bit streams encoded by or read by a machine or computer system that is encoding or decoding nucleic acids, raw data, files and compressed or decompressed zip files to be encoded or decoded into DNA stored data. Examples of UI's include, without limitation, a graphical user interface (GUI) and web-based user interface. Methods and systems of the present disclosure can be implemented by way of one or more algorithms. An algorithm can be implemented by way of software upon execution by the central processing unit 805. The algorithm can, for example, be used with a DNA index and raw data or zip file compressed or decompressed data, to determine a customized method for coding digital information from the raw data or zip file compressed data, prior to encoding the digital information.

Chemical methods involved in the systems and methods described herein are described in U.S. application Ser. No. 16/414,758 entitled "COMPOSITIONS AND METHODS FOR NUCLEIC ACID-BASED DATA STORAGE", filed May 16, 2019 and published as U.S. Publication No. 2020/0193301; and U.S. application Ser. No. 17/012,909 entitled "CHEMICAL METHODS FOR NUCLEIC ACID-BASED DATA STORAGE", filed Sep. 4, 2020, each of which is hereby incorporated by reference in its entirety.

Ligation may be used to attach sequencing adapters to a library of nucleic acids. For example, the ligation may be performed with common sticky ends or staples at the ends of each member of the nucleic acid library. If the sticky end or staple at one end of the nucleic acids is distinct from that of the other end, then the sequencing adapters may be ligated asymmetrically. For example, a forward sequencing adapter may be ligated to one end of the members of the nucleic acid library and a reverse sequencing adapter may be ligate to the other end of the members of the nucleic acid library. Alternatively, blunt-ended ligation may be used to attach adapters to a library of blunt-ended double-stranded nucleic acids. Fork adapters may be used to asymmetrically attach adapters to a nucleic acid library with either blunt ends or sticky ends that are equivalent at each end (such as A-tails).

Nucleic acid amplification may be executed with polymerase chain reaction, or PCR. In PCR, a starting pool of nucleic acids (referred to as the template pool or template) may be combined with polymerase, primers (short nucleic acid probes), nucleotide tri phosphates (such as dATP, dTTP, dCTP, dGTP, and analogs or variants thereof), and additional cofactors and additives such as betaine, DMSO, and magnesium ion. The template may be single stranded or double stranded nucleic acids. The primer may be a short nucleic acid sequence built synthetically to complement and hybridize to a target sequence in the template pool. Though "PCR" may typically refer to reactions specifically of said form, it may also be used more generally to refer to any nucleic acid amplification reaction.

High-throughput, single-molecule PCR may be useful for amplifying a pool of distinct nucleic acids that may interfere with each other. For example, if multiple distinct nucleic acids share a common sequence region, then recombination between the nucleic acids along this common region may occur during the PCR reaction, resulting in new, recombined nucleic acids. Single-molecule PCR would prevent this potential amplification error as it compartmentalizes distinct nucleic acid sequences from each other so they may not interact. Single-molecule PCR may be particularly useful for preparing nucleic acids for sequencing. Single-molecule PCR mat also be useful for absolute quantitation of a number of targets within a template pool. For example, digital PCR (or dPCR), uses the frequency of distinct single-molecule PCR amplification signals to estimate the number of starting nucleic acid molecules in a sample.

In some implementations of PCR, a group of nucleic acids may be non-discriminantly amplified using primers for primer binding sites common to all nucleic acids. For example, primers for primer binding sites flank all nucleic acids in a pool. Synthetic nucleic acid libraries may be created or assembled with these common sites for general amplification. However, in some implementations, PCR may be used to selectively amplify a targeted subset of nucleic acids from a pool, for example, by using primers with primer binding sites that only appear on said targeted subset of nucleic acids. Synthetic nucleic acid libraries may be created or assembled such that nucleic acids belonging to potential sub-libraries of interest all share common primer binding sites on their edges (common within the sub-library but distinct from other sub-libraries) for selective amplification of the sub-library from the more general library.

Affinity-tagged nucleic acids may be used as sequence specific probes for nucleic acid capture. The probe may be designed to complement a target sequence within a pool of nucleic acids. Subsequently, the probe may be incubated with the nucleic acid pool and hybridized to its target.

Synthetic nucleic acid libraries may be created or assembled with common probe binding sites for general nucleic acid capture. These common sites may be used to selectively capture fully assembled or potentially fully assembled nucleic acids from assembly reactions, thereby filtering out partially assembled or mis-assembled (or unintended or undesirable) bi-products. For example, the assembly may involve assembling a nucleic acid with a probe binding site on each edge sequence such that only a fully assembled nucleic product would contain the requisite two probe binding sites necessary to pass through a series of two capture reactions using each probe. For increased stringency, common probe binding sites may be included on each component of an assembly. In some implementations, nucleic acid capture may be used to selectively capture a targeted subset of nucleic acids from a pool. For example, by using probes with binding sites that only appear on said targeted subset of nucleic acids. Synthetic nucleic acid libraries may be created or assembled such that nucleic acids belonging to potential sub-libraries of interest all share common probe binding sites (common within the sub-library but distinct from other sub-libraries) for the selective capture of the sub-library from the more general library.

In some implementations, a library of nucleic acids may undergo lyophilization, for example, for preservation. Lyophilization is a dehydration process. Both nucleic acids and enzymes may be lyophilized. Lyophilized substances may have longer lifetimes. Additives such as chemical stabilizers may be used to maintain functional products (e.g., active enzymes) through the lyophilization process. Disaccharides, such as sucrose and trehalose, may be used as chemical stabilizers.

Nucleic acids may be designed to facilitate sequencing. For example, nucleic acids may be designed to avoid typical sequencing complications such as secondary structure, stretches of homopolymers, repetitive sequences, and sequences with too high or too low of a GC content. Certain sequencers or sequencing methods may be error prone. Nucleic acid sequences (or components) that make up synthetic libraries (e.g., identifier libraries) may be designed with certain hamming distances from each other. This way, even when base resolution errors occur at a high rate in sequencing, the stretches of error-containing sequences may still be mapped back to their most likely nucleic acid (or component). Nucleic acid sequences may be designed with hamming distances of at least 1, 2, 3, 4, 5, 6, 7, 8, 9, 10, 11, 12, 13, 14, 15 or more base mutations. Alternative distance metrics from hamming distance may also be used to define a minimum requisite distance between designed nucleic acids.

Some sequencing methods and instruments may require input nucleic acids to contain particular sequences, such as adapter sequences or primer-binding sites. These sequences may be referred to as "method-specific sequences". Typical preparatory workflows for said sequencing instruments and methods may involve assembling the method-specific sequences to the nucleic acid libraries. However, if it is known ahead of time that a synthetic nucleic acid library (e.g., identifier library) will be sequenced with a particular instrument or method, then these method-specific sequences may be designed into the nucleic acids (e.g., components) that comprise the library (e.g., identifier library). For example, sequencing adapters may be assembled onto the members of a synthetic nucleic acid library in the same reaction step as when the members of a synthetic nucleic acid library are themselves assembled from individual nucleic acid components.

Nucleic acids may be designed to avoid sequences that may facilitate DNA damage. For example, sequences containing sites for site-specific nucleases may be avoided. As another example, UVB (ultraviolet-B) light may cause adjacent thymines to form pyrimidine dimers which may then inhibit sequencing and PCR. Therefore, if a synthetic nucleic acid library is intended to be stored in an environment exposed to UVB, then it may be beneficial to design its nucleic acid sequences to avoid adjacent thymines (i.e., TT).

Methods of Computing with Identifiers

It may be possible to perform computations on data encoded in an identifier library using chemical operations. It may be advantageous to do so because such operations may be performed on any subset of an entire archive, or the entire archive, in a parallelized manner. Second, the computations may be performed in vitro without decoding the data thus ensuring secrecy while allowing computation. In one embodiment, computations involving Boolean logical operations such as AND, OR, NOT, NAND and more may be performed on bitstreams encoded using identifiers that represent each bit position where the presence of an identifier encodes the bit-value of '1' and the absence of an identifier encodes the bit-value of '0'.

In one embodiment, all identifiers are constructed as single stranded nucleic acid molecules (or initially as double stranded nucleic acid molecules and then isolated into single stranded form). For any single stranded identifier x, we denote an identifier that is a reverse complement of x by x*. For any set of single stranded identifiers S, we denote the set of reverse complements of each identifier in S as S*. We denote by U the set of all possible single-stranded identifiers in a library, and by U* the set of its reverse complements. We call these sets the universe and universe*. By $U_s$ and $U_s^*$, we denote a second pair of universe and universe* sets, such that each identifier in these sets is augmented with an additional nucleic acid sequence, known as a search region, that may be targeted or selected by chemical methods.

Computation on a given identifier library may be implemented by a sequence of chemical operations, involving hybridization and cleavage. Abstractions of these operations are described below. Each operation takes as an input a pool of identifiers, performs an operation, and returns as an output a pool of identifiers.

The operation single(X) takes a pool of identifiers (double stranded and/or single stranded) and returns only the single stranded nucleic acid identifiers (removing all double stranded identifiers). The operation double(X) takes a pool of identifiers (double stranded and/or single stranded) and returns only the double stranded identifiers (removing all single stranded identifiers). The operations make-single(X) and make-single*(X) converts all double stranded nucleic acid identifiers into their single stranded forms. (The starred version returns the negative strand while the non-starred version returns the positive strand.) The operation get(X, q) returns a pool of all identifiers matching query q. When q="all", the query matches and operates on all identifiers. The operation delete(X, q) deletes all identifiers (double stranded or single stranded) that satisfy query q. Queries may be implemented via random access as described previously. The operation combine(P, Q) returns a pool containing all identifiers in P or Q. We define the operation assign(X, Y) which assigns the result of Y to the variable name X. For brevity, we also denote this operation in the following form: X=Y. We assume that assignment operations execute under ideal conditions allowing variables to be reused without any "contamination" issues.

In the sequel, we assume that bitstreams a and b both of length l have been written into double stranded identifier libraries dsA and dsB, respectively, and that we are interested in computing on some sub-bitstreams $s = a_i \ldots a_j$ and $t = b_i b_j$, with the result of the computation to be stored in the sub-bitstream s. That is, we assume the following operations have been executed in the specified order initially, denoted by the initialize(dsA, dsB, s, t) operation:

| 1 | A = make-single(dsA) |
| 2 | A* = make-single*(dsA) |
| 3 | B = make-single(dsB) |
| 4 | B* = make-single*(dsB) |
| 5 | P = get(A, "s") |

| | |
|---|---|
| 6 | Q = get(B*, "t") |
| 7 | A = delete(A, "s") |
| 8 | B* = delete(B*, "t") |

Figure 9:
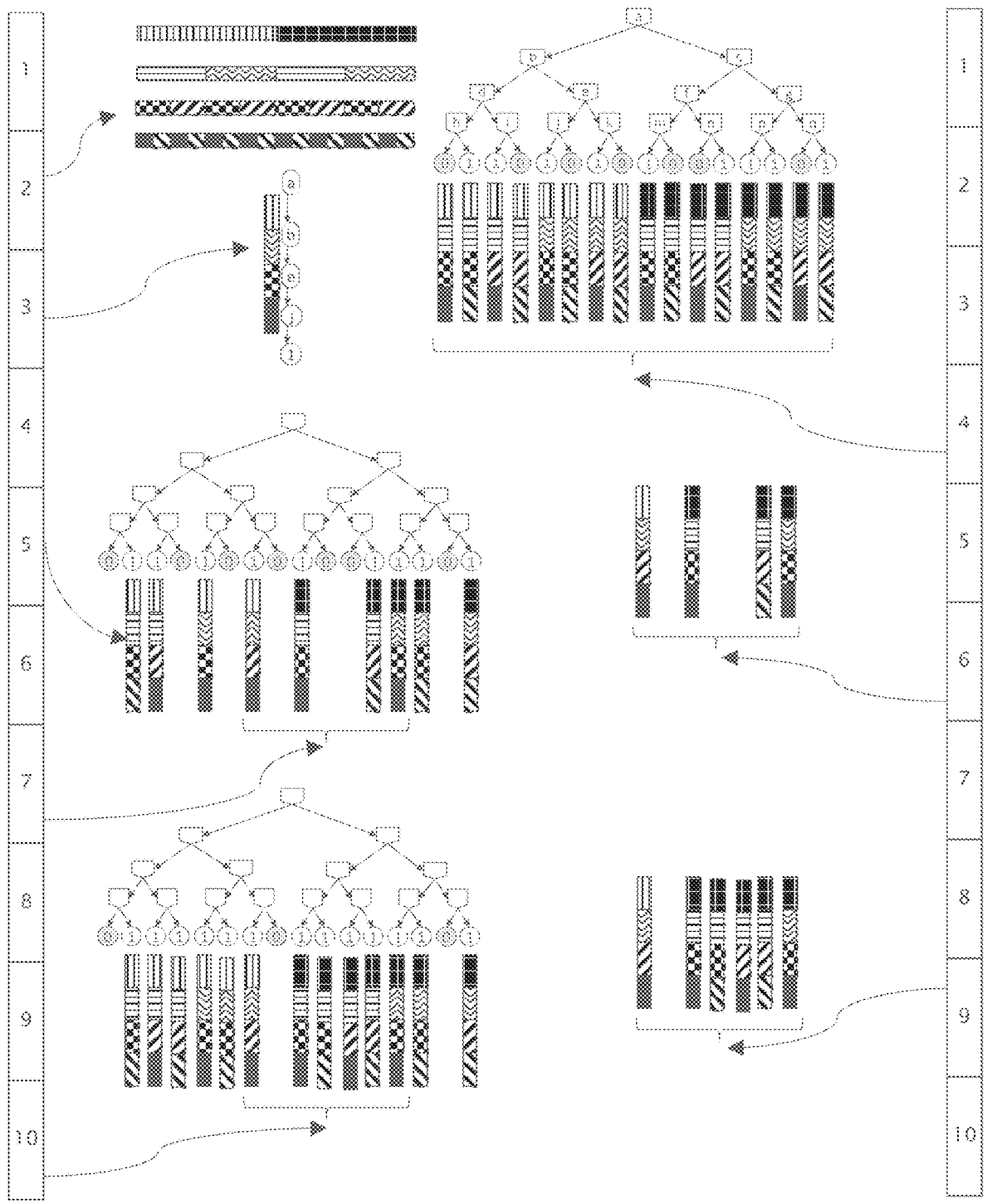
FIG. 9 shows an example of two source bitstreams and a universal identifier library prepared for computation using operations defined on identifier pools, according to an illustrative implementation.

FIG. 9 illustrates an example setup for computing with identifier libraries. The figure illustrates an example combinatorial space of identifiers drawn as an abstract tree data structure (labeled 4). In this example, each level of the tree chooses between two components (shown by label 2). Each path from the root of the tree corresponds to a unique identifier (as illustrated by the example in label 3), and determines its order (or rank). Label 4 shows the single stranded universal identifier library. Label 5 shows a single stranded identifier library that encodes a specific bitstream, called "a" for example. Label 7 shows a sub-bitstream of "a" called "s" comprising seven bits. Similarly, label 10 shows a sub-bitstream "t" of bitstream "b" of the same length. As described in the initialization procedure for computing initialize(dsA, dsB, s, t), the sub-bitstreams to be computed on are available in pools P and Q (labeled 6 and 9 respectively) and ready for computation.

The operation and(s, t), defined as the bitwise logical conjunction of the bits in bitstreams s and t, may be implemented using the sequence of operations below.

| | |
|---|---|
| 1 | R = combine(P, Q*) |
| 2 | S = double(R) |
| 3 | T = make-single(S) |
| 4 | T* = make-single*(S) |
| 5 | A = combine(A, T) |
| 6 | A* = combine(A, T*) |

The operation not(s), defined as the bitwise logical negation of the bits in bitstream s, may be implemented using the sequence of operations below:

| | |
|---|---|
| 1 | R = get(U*, "s") |
| 2 | S = combine(P, R) |
| 3 | T = single(S) |
| 4 | V = make-single(T) |
| 5 | A = combine(A, V) |
| 6 | A* = combine(A*, T) |

The operation or(s, t), defined as the bitwise logical disjunction of bits in bitstreams s and t, may be implemented using the sequence of operations below:

| | |
|---|---|
| 1 | R = get(B, "t") |
| 2 | A = combine(A, R) |
| 3 | A* = combine(A*, Q*) |

The operation n and(s, t), defined as the bitwise logical negation of the conjunction of the bits in bitstreams s and t, may be implemented using the sequence of operations below.

| | |
|---|---|
| 1 | R = combine(P, Q*) |
| 2 | S = single(R) |
| 3 | T = make-single(S) |
| 4 | T* = make-single*(S) |
| 5 | A = combine(A, T) |
| 6 | A* = combine(A, T*) |

In one embodiment, the operation single(X) may involve first combining X with either $U_s$ or $U_s^*$ so that the single stranded identifiers from X hybridize to the universal identifiers. Moreover, because the universal identifiers in $U_s$ and $U_s^*$ have a special search region, these molecules that hybridize to the universal identifiers may be accessed in a targeted manner.

In one embodiment, the operation double(X) may involve treating the identifiers in X with a single-stranded specific nuclease, such as S1 nuclease, and then running the resulting pool of DNA on a gel to isolate only identifiers that were not cleaved (and hence fully double-stranded).

Figure 10:
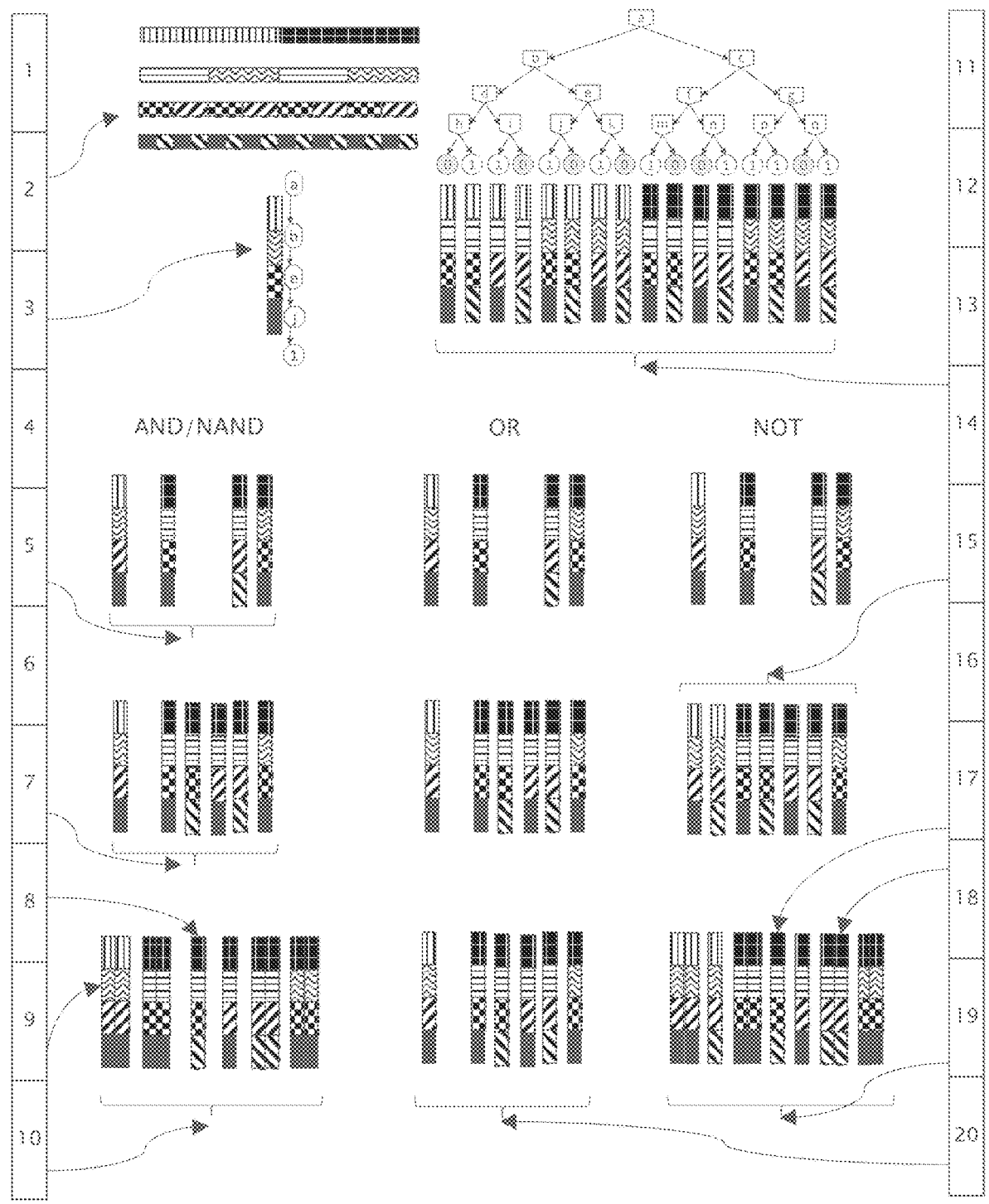
FIG. 10 shows the inputs to and results of three examples of logical operations performed on a pool of identifiers illustrating how identifier libraries may be used as a platform for in vitro computation, according to an illustrative implementation.

FIG. 10 illustrates an example of how logical operations may be performed on bitstreams "s" and "t" encoded by identifier libraries. In this figure, we use a universal library (labeled 14) such that it is complementary to the pool being computed with. The column labeled AND/NAND shows how one may compute the conjunction of bitstreams "s" and "t" (labeled 5 and 7 respectively). We assume that the pools are reformatted using the correct universal library (U or U*). When the two pools are combined, complementary single stranded identifiers hybridize forming double identifiers, as shown (label 9, for example). The collection of double stranded identifiers in the resulting pool (labeled 10) encodes the result of the AND computation: separating out the double stranded products gives an identifier library representation of and(s, t). Alternatively, separating out the single stranded products gives the identifier library representation of nand(s, t). The column labeled OR shows how one may compute the disjunction of bitstreams "s" and "t". When the pools containing the identifiers representing "s" and "t" are combined, the resulting library contains the representation of or(s, t). The column labeled NOT shows how one may compute the negation of the bitstream "s". Here, the single stranded identifier library representing the bitstream "s" is combined with the complementary universal identifier library (labeled 15). As a result (labeled 19), all the double stranded products formed (labeled 18, for example) represent the "1" bits in "s" and may be discarded. The remaining single stranded products (for example, labeled 17) represent the "0" bits in "s" and thus correspond to the "1" bits in not(s). These single stranded products give the identifier library representation of not(s) and may be used for further computation.

Methods of Data Randomization, Cryptography, and Authentication with DNA

The ability to generate and store random bitstreams using DNA may have applications in computations in cryptography and combinatorial algorithms. Many encryption algorithms, for example DES, require the use of random bits to guarantee security. Other encryption algorithms, for example AES, require the use of cryptographic keys. Typically, these random bits and keys are generated using a secure source of randomness, because any systematic patterns or biases in the random bits or the keys may be exploited to attack and break encrypted messages. Furthermore, the keys used to encrypt are typically required to be archived for decryption. The strength of the security of encryption methods is dependent on the length of the key used in the algorithm: generally the longer the key, the stronger the encryption. Methods like one-time-pads are one of the most secure encryption methods, but find limited application due to their lengthy key requirement.

The methods described in this document may be used to generate and archive extremely large collections of random keys that may be tens, hundreds, thousands, tens of thousands, or more bits in length. In one implementation, a nucleic acid library may be generated in which each nucleic acid molecule satisfies the following design: it has a length of n bases with a variable region of k<n bases. The bases in the variable region are allowed to be chosen at random during the construction of the library. For example, n may be 100 and k may be 80; thus, a library of size $10^{50}$ different molecules may potentially be generated. A random sample of such a library, of size 1000 molecules for example, may be sequenced to obtain up to 1000-bit random keys which may be used for encryption.

In another implementation, nucleic acid keys (nucleic acid molecules representing keys) described above may be attached to identifiers yielding an ordered collection of key sets. The ordered key sets may be used to synchronize the order in which keys are used by various parties in an encryption context. For example, an identifier library may be constructed combinatorially using a product scheme to obtain $10^{12}$ unique identifiers. Using microfluidic methods, each identifier may be collocated with a nucleic acid key, and assembled to form a nucleic acid sample comprising a unique identifier and a random key. Because the identifiers in the identifier library are ordered, keys may now be ordered and accessed and sequenced in any specified order.

In another implementation, keys attached to identifiers may be used to instantiate a random function that maps an input identifier to a string of random bits. Such random functions may be useful in applications that require functions that are easy to compute the value of but difficult to invert from a given value, such as hashing. In such an application, a library of keys, each assembled with a unique identifier, is used as the random function. When a value is to be hashed, it is mapped to an identifier. Next, the identifier is accessed from the key library using random access methods, such as hybridization capture or PCR. The identifier is attached to a key comprising sequences of random bases. This key is sequenced and translated into a string of bits and is used as the output of the random function.

Because nucleic acid molecular libraries may be cheaply and quickly copied, and because they may be covertly transported in small volumes, nucleic acid key sets generated as described above may be useful in contexts where a large number of encryption keys must be periodically distributed in a secure and covert way among multiple parties that are not geographically collocated. In addition, the keys may be reliably archived for extremely long periods of time enabling the secure storage of encrypted archived data.

FIGS. 11-16 illustrate implementations of methods for creating, storing, accessing, and using random or encrypted data stored in DNA. DNA is depicted as strings comprising grey and black bars and symbols. Each depicted DNA represents a distinct species. A "species" is defined as one or more DNA molecule(s) of the same sequence. If "species" is used in a plural sense, then it may be assumed that every species in the plurality of species has a distinct sequence, though sometimes this is made explicit by writing "distinct species instead of "species".

Figure 11:
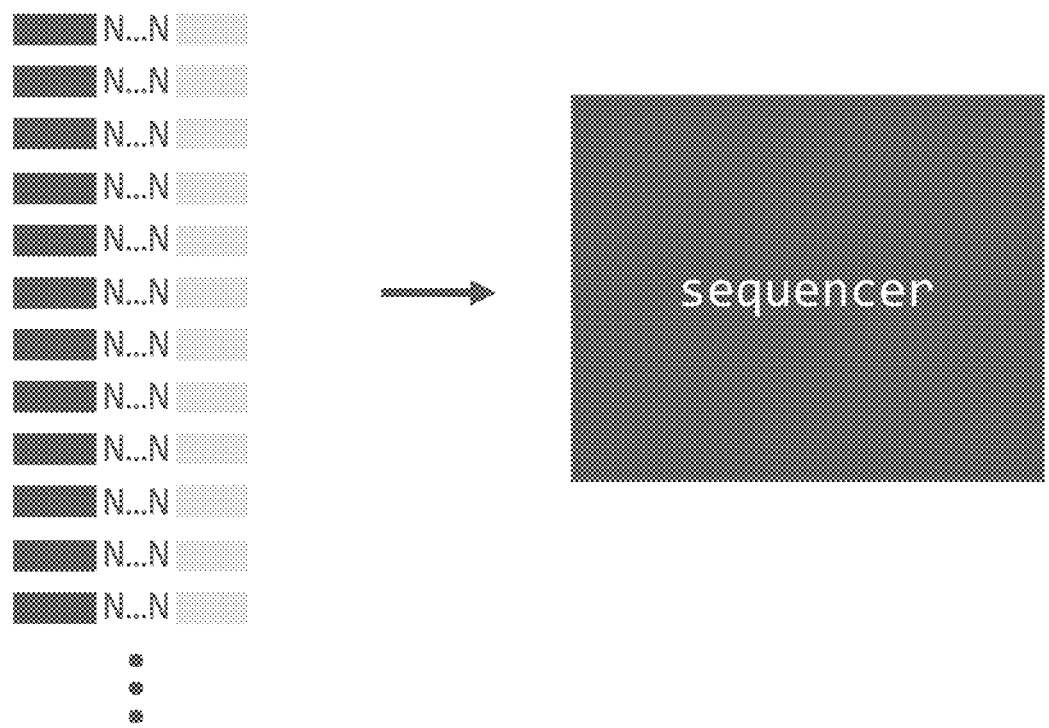
FIG. 11 shows an example method for generating entropy that may be used to create random bit strings, according to an illustrative implementation.

FIG. 11 depicts an example of an entropy (or random data) generator using a large combinatorial space of DNA and a sequencer. The method begins with a random pool of DNA species, referred to as a seed. The seed should ideally contain a uniform distribution of every species of a defined combinatorial set of DNA, for example, all DNA species with 50 bases (with 450 members). However, the full combinatorial space may be too large for every member to be represented in the seed, and so it is permissible that the seed contain a random subset of the combinatorial space instead of the entire combinatorial space. The seed species may be designed to have common sequences on the edges (the black and light grey bars) and then distinct sequences in the middle (N . . . N). Degenerate oligonucleotide synthesis strategies may be used to manufacture this starting seed in a rapid and inexpensive manner. The common edge sequences may enable amplification of the seed with PCR or compatibility with certain read-out (or sequencing) methods. As an alternative to degenerate oligonucleotide synthesis, combinatorial DNA assembly (multiplexed in one reaction) may also be used to rapidly and inexpensively generate a seed. The sequencer randomly samples species from the seed, and it does so in a random order. Because there is uncertainty in the species being read by the sequencer at any given time, the system may be classified as an entropy generator, and it may be used to generate random numbers or random streams of data, for example, as encryption keys.

Figure 12A:
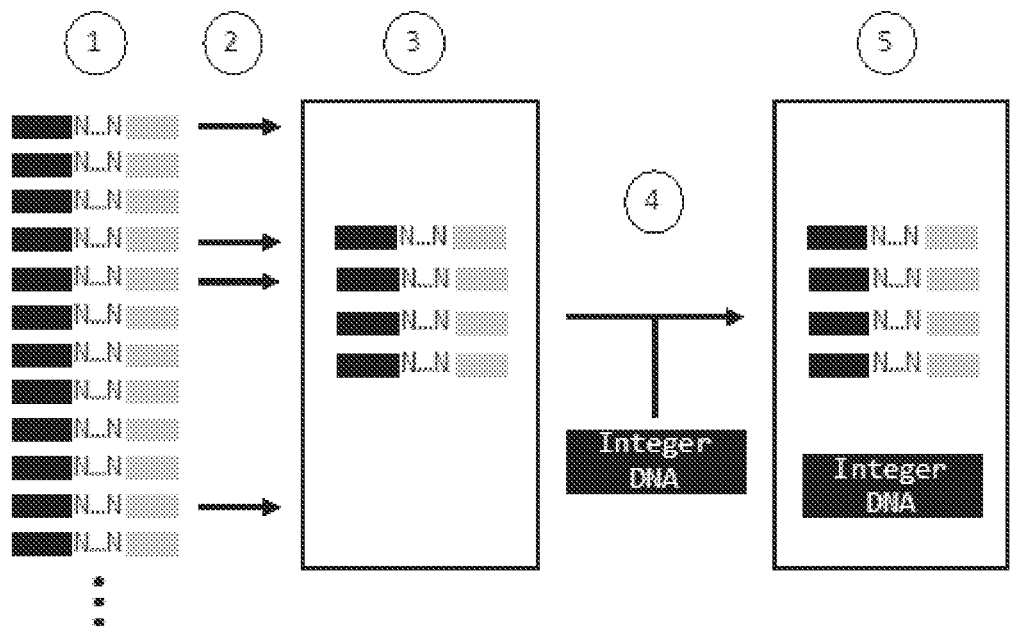
FIGS. 12A-12C show an example method for generating and storing entropy (random bit strings), according to an illustrative implementation.

FIG. 12A illustrates an example schematic of a method for storing randomly generated data in DNA. It begins with (1) a large random pool of DNA species, referred to as a seed. The seed should ideally contain a uniform distribution of every species of a defined combinatorial set of DNA, for example, all DNA species with 50 bases (with $4^{50}$ members). However, the full combinatorial space may be too large for every member to be represented in the seed, and so it is permissible that the seed contain a random subset of the combinatorial space. The seed may itself be generated from degenerate oligonucleotide synthesis or combinatorial DNA assembly. (2) Random data (or entropy) is generated by taking random subset of the species in the seed. For example, this may be accomplished by taking a proportional, fractional volume of the seed solution. For example, if the seed solution consists of an estimated 1 million species per microliter (uL), then a random subset of approximately 1 thousand species may be selected by taking a 1 nanoliter (nL) aliquot from the seed solution (assuming it is well-mixed). Alternatively, a subset may be selected by flowing an aliquot of the seed solution through a nanopore membrane and collecting the species only that pass the membrane. Counting the number of species that pass through the membrane may be achieved by measuring the voltage difference across the nanopores. This process may continue until a desirable number of signatures is detected (for example 100, 1000, 10000, or more species signatures). As another alternative method, single species may be isolated in small droplets (for example, with oil emulsions). The small droplets with single species may be detected by a fluorescent signature and sorted by a series of microfluidic channels into a collection chamber. (3) We may refer to each selected species as an identifier and, further, we may refer to the full subset of species selected as the "random identifier library" or RIL. To stabilize the information in the RIL and protect it from degradation, the RIL may be amplified with PCR primers that bind to common sequences on the ends of the species. To determine the identifiers in the RIL (and hence the data stored within), the RIL may be sequenced. True identifiers may be defined by the species in the sample with enrichment above a defined noise threshold. (4) Once the data contained in the RIL is determined, extra error checking and error correction species may be added to the RIL. For example, "integer DNA" that contains information on how many identifiers to expect (for example a checksum or a parity check) may be added to the RIL. The integer DNA may allow one to know how deeply to sequence the RIL in order to recover all of the information.

Figure 12B:
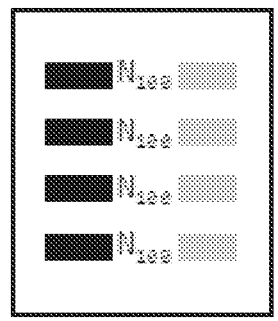
Figure 12C:
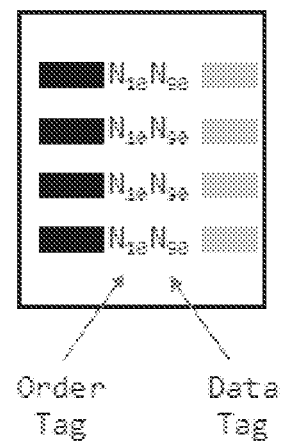

A RIL may be barcoded with a unique DNA tag. Several barcoded RILs may then be pooled together such that any given RIL may be individually accessed with a hybridization assay (or PCR) against its unique DNA tag. The unique DNA tags may be combinatorially assembled or synthesized and then assembled onto their corresponding RILs. FIG. 12B shows an example RIL comprising 4 species each containing one hundred random bases. The combinatorial space of possible species is $4^{100}$ and hence the RIL may contain $\log_2 (4^{100}$ choose4)≈725 bits of information. FIG. 12C also shows an example RIL comprising 4 species each containing one hundred random bases. As an alternative to storing the information in the particular unordered combination of 4 species chosen out of a combinatorial space of $4^{100}$ (as in FIG. 12B), the final 90 random bases of each species may be reserved to store)$\log_2(4^{90})$=180 bits of information, while the first 10 random bases may be reserved to establish a relative order between information stored in each of the 4 species. The relative order may be defined by a lexicographical ordering of the 10-base strings based on a defined ordering of the 4 bases (similar to the way in which words in the English language are ordered according to the order of letters in the alphabet). This method for assigning information to a RIL may be computationally faster to map to a binary string than the method described in FIG. 12B.

In the previous figure (FIG. 12A-C), we discuss a strategy for barcoding multiple RILs and pooling them together. In doing so, an input-output mapping is created wherein the inputs correspond to barcode hybridization probes (for accessing the individual RILs) and outputs correspond to random data strings (encoded by the targeted RIL). Whereas in this method, pre-defined barcodes are assembled to random data for retrieval from a combined pool, FIG. 13A demonstrates a different method for creating input-output mappings between nucleic acid probes and random data strings where the barcodes (for accessing the data) are generated randomly along with the random data itself. For example, the barcode may be a pair of short sequences of DNA that may appear on both edges of one or multiple species. In this implementation, the combinatorial space of the possible barcodes may be small compared to the total number all possible species in a pool such that each barcode is, by chance, associated with one or more species. For example, if a barcode is 3 bases on each edge of a random DNA sequence in a species (flanked by common sequences), then there are $4^6$=4096 possible barcodes and hence $4^6$=4096 primer pairs that may be built to access them (corresponding to 12-bit inputs). If a pool of DNA is selected such that it has approximately 400K species, then each barcode may be associated with approximately 100 species on average. In this implementation, RILs are defined by the subset of species associated with each barcode. Following the preceding example, if each species comprises 25 random bases (or random sequences) aside from the bases (or sequences) used for barcoding, then a barcode associated with a RIL of 100 species may contain up to $\log_2(4^{25}$ choose100)≈4475 bits of information.

Figure 13A:
FIGS. 13A-13B show an example method for organizing and accessing random bit strings using inputs, according to an illustrative implementation.
Figure 13B:
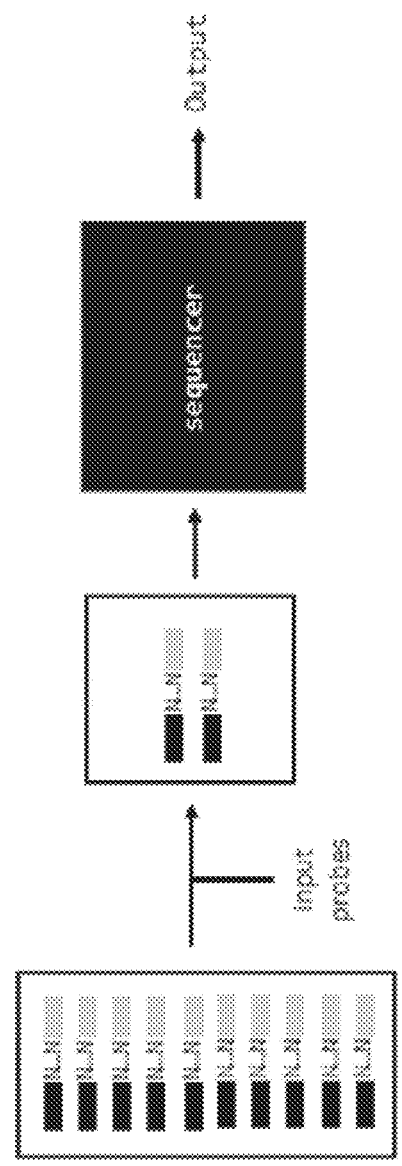

FIG. 13B demonstrates an implementation of a scheme for accessing and reading stored random data from a pool of barcoded RILs. The sequencer (or reader) may further comprise a function to manipulate the sequence data prior to returning the output. A hash function, for example, may make it difficult to use the output data string to perform a reverse chemical query and find its inputs. This functionality may be useful, for example, if the inputs are keys or credentials used for authentication.

The method of generating and storing query-able (or accessible) random strings of data may be particularly useful for generating and archiving encryption keys (generated from the random data strings). Each input may be used to access a different encryption key. For example, each input may correspond to a particular user, time range, and/or project in a private archival database. The encrypted data in the private archival database (potentially amounting to a very large amount of data) may be stored in conventional medium by an archival service provider while the encryption keys may be stored in DNA by the owner. Moreover, the potential latency and sophistication required to perform the chemical access protocol for a particular input may heighten the security barrier of the encryption method against hacking.

Figure 14:
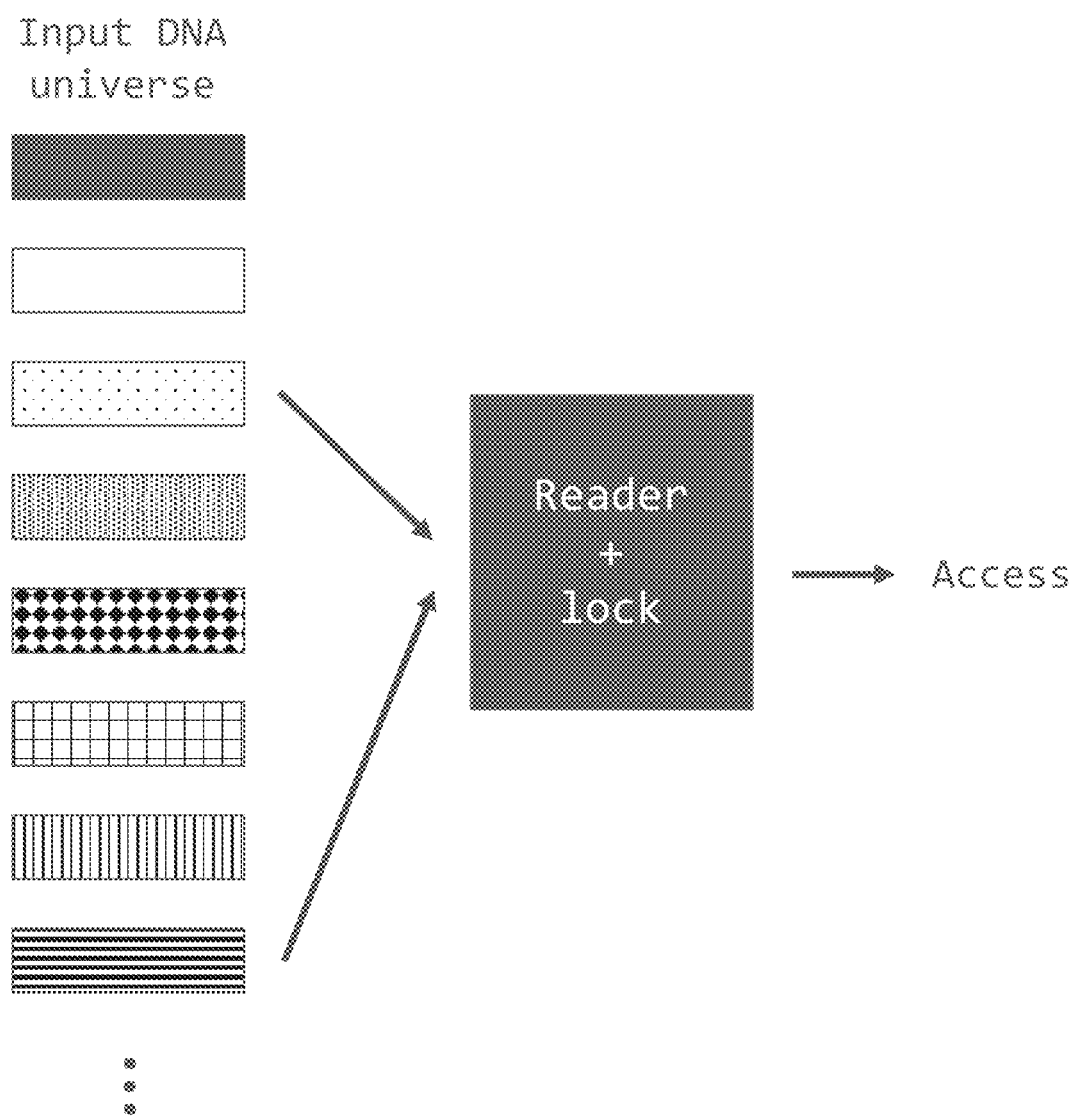
FIG. 14 shows an example method for securing and authenticating access to artifacts using physical DNA keys, according to an illustrative implementation.

FIG. 14 illustrates an example system for securing and authenticating access to an artifact. The system requires a physical key comprising a particular combination of species of DNA taken from a large pool of possible species. A target combination of species, also referred to as an "identifier key", may for example be generated automatically by a combinatorial microfluidic-channel, electrowetting, or printing device, or manually by pipetting. A reader or sequencer with a built-in lock verifies a matching identifier key and enables access to an artifact. Alternatively, the reader may behave as a credential-token system where, instead of directly unlocking access to an artifact, it returns a token that may be used to access the artifact. The token may be generated, for example, by a built-in hashing function within the reader, wherein the hashing function is applied to read or sequence data from the reader electronically. For example, the reader comprises a processor configured to execute the steps of a program on a processor-readable medium, the steps involving taking in the read or sequence data, applying one or more mathematical or logical operations to the data, and outputting a hashed value or hashed token.

Figure 15:
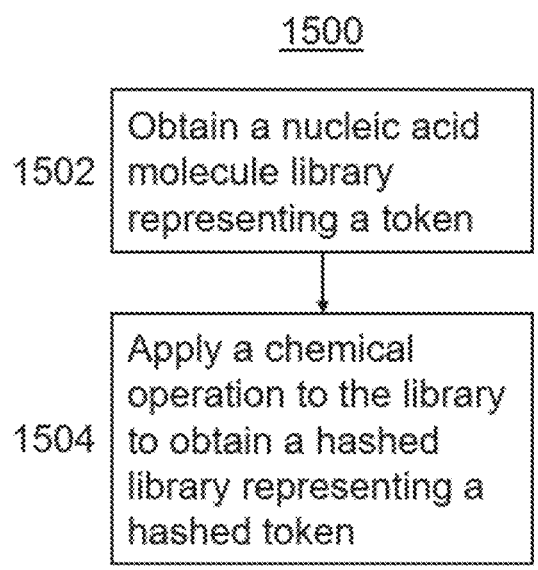
FIG. 15 shows a flowchart describing a method for preparing a nucleic acid library for authentication, according to an illustrative implementation.

Rather than apply the hashing function electronically within the reader or otherwise after sequencing the identifiers, a hashing function may be applied chemically via one or more reactions applied to the identifier library to generate a hashed library prior to sequencing or reading of the then hashed identifiers. This approach is advantageous, as it represents an air-gapped approach for higher security of the information encoded by the identifiers, as only the hashed identifiers are sequenced or read, so the sequence data of the original library of identifiers is not revealed. FIG. 15 shows a flowchart describing a method 1500 for preparing a library of nucleic acid molecules for use in security and authentication. The method 1500 involves steps 1502 and 1504. Step 1502 involves obtaining the library of nucleic acid molecules representing a security token. Step 1504 involves applying a chemical operation to the library representing the security token to obtain a hashed library of nucleic acid molecules representing a hashed token.

The chemical operation may be designed to effect one or more Boolean functions on the security token. For example, the Boolean functions described above in relation to FIGS. 9 and 10 may be applied to the library and thus the token it represents. These Boolean functions may constitute a hash function applied chemically to the library to obtain the hashed library representing the hashed token. The hashed library may be a subset of the original library, the subset being determined by selecting a portion of the nucleic acid molecules of the library.

In some implementations, method 1500 further comprises sequencing at least a portion of the nucleic acid molecules of the hashed library to obtain a sequencing readout. Further, method 1500 may involve comparing the sequencing readout to a database or look-up table to determine a presence or absence of a matching sequence. Based on the presence or absence of the matching sequence in the sequencing readout, access to a secured asset or location may be granted to denied. Suitable types of sequence include Sanger sequencing, high throughput sequencing, shotgun sequencing, and nanopore sequencing.

Rather than sequencing the hashed library, a validation function may be applied to authenticate the hashed token without the need for sequencing the full library. The validation function is performed by one or more additional chemical operations on the hashed library to produce an output molecule if the hashed token matches a reference sequence. The chemical operations may have the effect of performing Boolean logic, such as that described above in relation to FIGS. 9 and 10, to the hashed token. An assay is then used to determine a presence or absence of the output molecule. The chemical operations of the validation function may involve nested PCR, PCR with target-specific primers, applying a set of probes (e.g., affinity tagged probes or degradation targeting probes), or applying an enzyme or protein that interacts with the nucleic acids of the hashed library. For example, the chemical operations of the validation function may have the effect of comparing the hashed token to a reference pattern/sequence by applying primers to the hashed library, where the primers are designed to only hybridize to nucleic acid molecules having a sequence that matches the reference pattern. Another example involves comparing or evaluating the hashed token by using a zinc finger nuclease, transcription activator-like effector nuclease (Talen), or CRISPR-associated protein, such as Cas9, that targets nucleic acid molecules having a sequence corresponding to the reference pattern. These proteins may cleave the targeted nucleic acid molecules to create a fragment. Cas9 specifically can use a guide RNA having complementarity to target nucleic acids. Output molecules may be any of a small molecule, a nucleic acid molecule, a nucleic acid molecule having a particular sequence, a nucleic acid fragment of one of the nucleic acids of the library, a protein, an enzyme, a functionalized protein, a tagged molecule, or a molecule configured to decay in a short period of time. For example, the output molecule is an RNA (e.g., an RNA from the library) which degrades via methylation of uracil to thymine or oxidative degradation of uracil, processes which modify the sequence of the RNA, giving the RNA a limited lifetime of sequence fidelity.

For example, PCR, reverse transcription PCR (RT-PCR), qPCR, affinity tagging, fluorimetry, or electrophoresis may be used as the assay for completing the validation function. Fluorimetry may be particularly useful when the output molecule is or is tagged with a fluorophore. RT-PCR is useful for assaying RNA as the output molecule, in order to produce complementary DNA (cDNA) that is more chemically stable than the RNA. The assay may also or alternatively be used to verify the chemical identity of the output molecule. The method may further involve, based on the assay results, granting or denying access to a secured asset or location. The method may further involve, based on the assay results, determining authenticity of an artifact associated with the library.

In some implementations, the library comprises a unique molecular barcode. The library may be lyophilized for stabilized storage. The security token may be unique to a user of the token. The security token may encode a message, a codeword, randomized codeword/key/string, an identity, or a currency value. The token may be part of a two-factor authentication system, wherein a password is entered to log-in to a system, and the library is presented, hashed, and validated to confirm or deny access to the system. The library may be configured to decay after a period of time. For example, the library is RNA (e.g., an RNA from the library) which degrades via methylation of uracil to thymine or oxidative degradation of uracil, processes which modify the sequence of the RNA, giving the RNA a limited lifetime of sequence fidelity.

In some implementations, the library is collocated with an artifact, and the security token is unique to the artifact. For example, the artifact is a container configured to encapsulate the library, such as a well, a droplet, a spot, a sealed container, a gel, a suspension, or a solid matrix. Other suitable artifacts include a fluid (e.g., liquids, gases, oil, ink, compressed gas, or drug), an organism, a currency, or a document. When the artifact is a document, an ink or stamp containing the library is imprinted on the document.

The library may encode at least about a kilobit of information. The security token may comprise a plurality of symbols, and each symbol is represented by a distinct sequence of a nucleic acid molecule of the library. In some implementations, the library is randomly generated. For example, any of the random libraries described in relation to FIGS. 11-13 are employed. In some implementations, the security token is represented by the library of nucleic acid molecules via an encoding scheme wherein the token is mapped to a plurality of symbols having one of two possible symbol values, wherein a symbol of the plurality of symbols is represented by presence of a distinct nucleic acid molecule in the library if the symbol has a first symbol value of the two possible symbol values, and wherein the symbol is represented by absence of the distinct nucleic acid molecule if the symbol has a second symbol value of the two possible symbol values.

Methods of Tagging Artifacts and Tracking Entities with DNA

Identifier libraries dissolved in solvent may be sprayed, spread, dispensed, or injected into or on physical artifacts to tag them with information. Identifier libraries in solid form (e.g., lyophilized) may be deposited, electrostatically stuck, chemically bound, or aerosolized and sprayed into or on physical artifacts to tag them with information. For example, an unique identifier library may be used to tag distinct instances of a type of artifact. An identifier library tag on an artifact may act as a unique barcode or value, or it may contain more sophisticated information such as a product number, a manufacturing or shipping date, a location of origin, or any other information pertaining to the history of the artifact, for example a transaction list of previous owners. A primary advantage of using identifiers to tag artifacts is that the identifiers are undetectable, durable, and well suited to tag a vast number of artifact instances individually.

A physical object may be marked or painted with a sample of uniquely identifiable synthetic DNA. Even gas (e.g. compressed air) and liquid (e.g. ink or oil) can be tagged, which is not possible with conventional methods. If ink, for example the ink in a print cartridge or a pen, is tagged with unique DNA libraries and used to print or write on a document, then the authenticity of said document can be validated by swabbing the DNA from the document and sequencing it. Additionally, covert messages may be included in the ink that either supplement or validate the material in the document. The tags are discreet and can, for example, be used to identify if an object has moved through a certain physical space or interacted with another object. The tags are also quantitative and can therefore be used to verify if a certain object has been tampered with or diluted (if liquid or gaseous). For example, if a liquid is tagged with 1000 copies of a tag per mL, but it is later recovered at 100 copies per mL, then it may be inferred that the liquid was diluted. The tags and barcodes can be readily created and deployed. They can contain up to kilobits, or more, of information. They can be created by taking a subset of identifiers from a pre-fabricated combinatorial space of possible identifiers.

An identifier library can be readily generated and used as a token to gain access to a secure asset. The token can be small, for example, encoding a kilobit of information, but still secure. The identifier library representing the token can be created by taking a subset of identifiers from a pre-fabricated combinatorial space of possible identifiers. For example, the token may be given to an owner upon deposit and accepted upon withdrawal of an asset. Alternatively, the token may be created by the owner, like a physical key. Because of its physical nature, the token would not be subject to electronic theft or tampering. Similarly, because of its discreet nature, the token would be difficult to forge. Chemical methods may be used to hash or validate the token to prevent the token from ever entering an electronic or readable format. The hash function or the validation function can be performed using chemical operations, like Boolean logic gates described above in relation to FIGS. 9 and 10. For example, chemical logic gates like AND, OR, NOT, and NAND can be composed together to form a hash function such that it is intractable to infer an original token by sequencing its hashed token. The value of the hashed token is what may be matched to a database to determine authorization to an asset. Due to the irreversibility of the hash function, the database may be made viewed by unauthorized parties but still without compromising the security of the asset and the ability of the authorized party to access it. Additionally or alternatively, chemical logic gates can comprise a validation function for the token that can validate the token without requiring sequencing the DNA molecules that comprise it. For example, the validation function may be used to produce a particular output identifier if and only if the token matches an exact pattern. The presence of said identifier may be determined, for example, with an assay such as real-time PCR (qPCR), fluorimetry, or gel electrophoresis.

Figure 16:
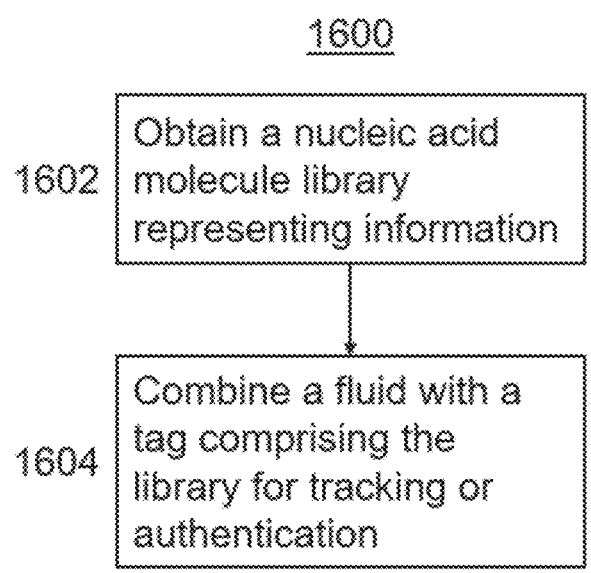
FIG. 16 shows a flowchart describing a method for tagging a fluid with a nucleic acid tag for tracking or authentication, according to an illustrative implementation.

FIG. 16 shows a flowchart describing a method 1600 for tagging a fluid for tracking or authentication. Method 1600 comprises steps 1602 and 1604. Step 1602 involves obtaining a library of nucleic acid molecules representing information. Step 1604 involves combining the fluid with a tag comprising the library to obtain a tagged fluid for tracking or authentication. For example, the tag comprising the library of nucleic acid molecules is dispersed approximately uniformly throughout the tagged fluid.

In some implementations, method 1600 further comprises sampling the library of nucleic acid molecules from the tagged fluid to obtain a sample. Sampling may involve swabbing the tag or the tagged fluid, extracting at least a portion of the library from the tagged fluid (e.g., by pipetting or drawing a volume from the fluid), or removing the tag from the tagged fluid (e.g., via a separation process such as filtration). In some implementations, the tag further comprises a magnetic bead, and sampling involves applying a magnet to the fluid to extract the tag via the magnetic bead. Method 1600 may further comprise sequencing the sample of nucleic acid molecules to obtain a sequencing readout. Any of the sequencing methods described above may be employed for this step. The sequencing readout may be transmitted to a computer system, such as the computer network described in FIG. 8. According to the methods described herein, the sequencing readout may be hashed using a hashing function to obtained hashed data for security of the information.

The library may encode at least about a kilobit of information. The amount of information may be scaled based on the size of the library and/or the fluid. In some implementations, the tag comprises a molecular barcode specific to the tag or the fluid. The information encoded by the library of nucleic acid molecules may be a message, such as an encrypted message. The information may represent a currency value. The tag may be part of a two-factor authentication system.

In some implementations, the fluid is an liquid, gas, oil, ink, compressed gas, or drug. The method 1600 may involve measuring a concentration of the tag in the tagged fluid to determine an amount of dilution. In some implementations, the tag is configured to decay or dilute within a period of time. For example, the period of time is initiated when the tag or fluid is accessed or sampled. For example, the nucleic acids of the tag are RNA which degrades via methylation of uracil to thymine or oxidative degradation of uracil, processes which modify the sequence of the RNA, giving the RNA a limited lifetime of sequence fidelity. Alternatively, the fluid is contained within a locked container, and, when the locked container is broken into, a reagent is released into the fluid to react with the tag.

The library of nucleic acid molecules may be an identifier library encoding information as described above. The information may comprise or be mapped to a plurality of symbols, and each symbol is represented by a distinct sequence of a nucleic acid molecule of the library. In some implementations, the library is a subset of a larger library. In some implementations, the library is randomly generated, as is described above in relation to FIGS. 11-13. In some implementations, the information is represented by the library of nucleic acid molecules via an encoding scheme wherein the information is mapped to a plurality of symbols having one of two possible symbol values, wherein a symbol of the plurality of symbols is represented by presence of a distinct nucleic acid molecule in the library if the symbol has a first symbol value of the two possible symbol values, and wherein the symbol is represented by absence of the distinct nucleic acid molecule if the symbol has a second symbol value of the two possible symbol values. For example, the two possible symbol values are 0 and 1, and nucleic acid molecules corresponding to symbols having the value 0 are absent from the tag, and nucleic acid molecules corresponding to symbols having the value 1 are present in the tag.

In another implementation, one or more physical locations may each be tagged with unique identifiers from an identifier library. For example, physical sites A, B, and C may be ubiquitously tagged with an identifier library. An entity, for example, a vehicle, person, or any other object, that visits site A or comes in contact with site A may, intentionally or not, pick up a sample of the identifier library. Later upon accessing the entity, the sample may be gathered from the entity and chemically processed and decoded to identify which site was visited by the entity. An entity may visit more than one site and may pick up more than one sample. A similar process may be used to identify some or all the sites visited by the entity if the identifier libraries are disjoint. Such a scheme may have an application in covert tracking of entities. Some advantages of using this scheme are that identifiers are undetectable unless specifically sought, may be designed to be biologically inert, and may be used to uniquely tag a vast number of sites or entities.

In another implementation, an identifier library may tag an entity. The entity may leave samples of the injected identifiers in sites that it visits. These samples may be gathered, processed and decoded to identify which entities may have visited a site.

EXAMPLES

Example 1: Encoding, Writing and Reading a Single Poem in DNA Molecules

Data to be encoded is a textfile containing a poem. The data is encoded manually with pipettes to mix together DNA components from two layers of 96 components to construct identifiers using the product scheme implemented with overlap extension PCR. The first layer, X, comprises 96 total DNA components. The second layer, Y, also comprises 96 total components. Prior to writing the DNA, the data is mapped to binary and then recoded to a uniform weight format where every contiguous (adjacent disjoint) string of 61 bits of the original data is translated to a 96 bit string with exactly 17 bit-values of 1. This uniform weight format may have natural error checking qualities. The data is then hashed into a 96 by 96 table to form a reference map.

Figure 17A:
FIGS. 17A and 17B show examples of encoding, writing, and reading data encoded in nucleic acid molecules.

The middle panel of FIG. 17A shows the two-dimensional reference map of a 96 by 96 table encoding the poem into a plurality of identifiers. Dark points correspond to a '1' bit-value and white points corresponded to a '0' bit-value. The data is encoded into identifiers using two layers of 96 components. Each X value and Y value of the table is assigned a component and the X and Y components are assembled into an identifier using overlap extension PCR for each (X,Y) coordinate with a '1' value. The data was read back (e.g., decoded) by sequencing the identifier library to determine the presence or absence of each possible (X,Y) assembly.

The right panel of figure FIG. 17A shows a two-dimensional heat map of the abundances of sequences present in the identifier library as determined by sequencing. Each pixel represents a molecule comprising the corresponding X and Y components, and the greyscale intensity at that pixel represents the relative abundance of that molecule compared to other molecules. Identifiers are taken as the top 17 most abundant (X, Y) assemblies in each row (as the uniform weight encoding guarantees that each contiguous string of 96 bits may have exactly 17 '1' values, and hence 17 corresponding identifiers).

Example 2: Encoding a 62824 Bit Textfile

Data to be encoded is a textfile of three poems totaling 62824 bits. The data is encoded using a Labcyte Echo® Liquid Handler to mix together DNA components from two layers of 384 components to construct identifiers using the product scheme implemented with overlap extension PCR. The first layer, X, comprises 384 total DNA components. The second layer, Y, also comprises 384 total components. Prior to writing the DNA, the data is mapped to binary and then recoded to decrease the weight (number of bit-values of '1') and include checksums. The checksums are established so that there is an identifier that corresponds to a checksum for every contiguous string of 192 bits of data. The re-coded data has a weight of approximately 10,100, which corresponds to the number of identifiers to be constructed. The data may then be hashed into a 384 by 384 table to form a reference map.

Figure 17B:
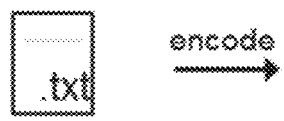

The middle panel of FIG. 17B shows a two-dimensional reference map of a 384 by 384 table encoding the text-file into a plurality of identifiers. Each coordinate (X,Y) corresponds to the bit of data at position X+(Y−1)*192. Black points correspond to a bit value of '1' and white points correspond to a bit value of '0'. The black points on the right side of the figure are the checksums and the pattern of black points on the top of the figure is the codebook (e.g., dictionary for de-coding the data). Each X value and Y value of the table may be assigned a component and the X and Y components are assembled into an identifier using overlap extension PCR for each (X, Y) coordinate with a '1' value. The data was read back (e.g., decoded) by sequencing the identifier library to determine the presence or absence of each possible (X, Y) assembly.

The right panel of FIG. 17B shows a two-dimensional heat map of the abundances of sequences present in the identifier library as determined by sequencing. Each pixel represents a molecule comprising the corresponding X and Y components, and the greyscale intensity at that pixel represents the relative abundance of that molecule compared to other molecules. Identifiers are taken as the top S most abundant (X, Y) assemblies in each row, where S for each row may be the checksum value.

While preferred implementations of the present invention have been shown and described herein, it will be obvious to those skilled in the art that such implementations are provided by way of example only. It is not intended that the invention be limited by the specific examples provided within the specification. While the invention has been described with reference to the aforementioned specification, the descriptions and illustrations of the implementations herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the implementations of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for preparing nucleic acid molecules for use in security and authentication of an artifact, the method comprising:
    obtaining a library of nucleic acid molecules encoding a security token, wherein the security token comprises a string of information which uniquely identifies the artifact; and
    applying a chemical operation to the library encoding the security token to obtain a hashed library of nucleic acid molecules encoding a hashed token.

2. The method of claim 1, wherein the chemical operation effects one or more Boolean functions on the security token.

3. The method of claim 2, wherein the one or more Boolean functions apply a hash function to the security token to obtain the hashed token encoded by the hashed library, wherein the hashed token is a hashed string of information.

4. The method of claim 1, further comprising:
sequencing at least a portion of the nucleic acid molecules of the hashed library to obtain a sequencing readout.

5. The method of claim 4, further comprising:
comparing the sequencing readout to a database or look-up table to determine a presence or absence of a matching sequence.

6. The method of claim 5, further comprising:
granting or denying access to a secured asset or location based on the determined presence or absence of the matching sequence, respectively.

7. The method of claim 4, wherein sequencing comprises any one of high-throughput sequencing, shotgun sequencing, or nanopore sequencing.

8. The method of claim 1, further comprising:
applying an additional chemical operation to the hashed library to produce an output molecule if the hashed token matches a reference sequence; and
determining a presence or absence of the output molecule via an assay.

9. The method of claim 8, wherein the assay is one of polymerase chain reaction (PCR), real-time PCR, reverse transcription PCR (RT-PCR), fluorimetry, and gel electrophoresis.

10. The method of claim 8, wherein the output molecule is a nucleic acid molecule of the hashed library, the nucleic acid molecule having a nucleic acid sequence which is distinct from sequences of other nucleic acid molecules in the hashed library.

11. The method of claim 8, further comprising:
granting or denying access to a secured asset or location based on the presence of the output molecule.

12. The method of claim 1, wherein the library comprises a unique molecular barcode.

13. The method of claim 1, wherein the security token comprises a randomly generated key.

14. The method of claim 1, wherein the library is lyophilized.

15. The method of claim 1, wherein the library is collocated with the artifact.

16. The method of claim 15, wherein the artifact is a fluid.

17. The method of claim 16, wherein the fluid is any one of an oil, an ink, a compressed gas, or a drug.

18. The method of claim 16, further comprising:
measuring a concentration of the library in the fluid to determine an amount of dilution.

19. The method of claim 15, wherein the artifact is an organism.

20. The method of claim 15, wherein the artifact is a document.

21. The method of claim 1, wherein the library is contained in any one of a well, a droplet, a spot, a sealed container, a gel, a suspension, or a solid matrix.

22. The method of claim 1, wherein the library is generated by selecting a subset of nucleic acid molecules from a pool of nucleic acid molecules.

23. The method of claim 1, wherein the security token is part of a two-factor authentication system.

24. The method of claim 1, wherein the string of information of the security token comprises a plurality of symbols, and each symbol is represented by a sequence of a nucleic acid molecule of the library, the sequence being distinct from sequences of other nucleic acid molecules in the library representing other symbols.

25. The method of claim 1, wherein the library is randomly generated.

26. The method of claim 1, wherein the security token is encoded by the library of nucleic acid molecules via an encoding scheme wherein the security token is mapped to a plurality of symbols having one of two possible symbol values, wherein a symbol of the plurality of symbols is represented by presence of a distinct nucleic acid molecule in the library if the symbol has a first symbol value of the two possible symbol values, and wherein the symbol is represented by absence of the distinct nucleic acid molecule if the symbol has a second symbol value of the two possible symbol values.

27. The method of claim 1, wherein the security token comprises at least a kilobit of information.

28. The method of claim 1, wherein the security token is unique to a user.

29. The method of claim 1, wherein the hashed library is a subset of the library.

30. The method of claim 1, wherein the string of information comprises symbols each encoded by a presence or absence of a corresponding nucleic acid molecule in the library.

* * * * *